United States Patent
Peterson et al.

(10) Patent No.: US 7,208,647 B2
(45) Date of Patent: Apr. 24, 2007

(54) PROCESS FOR THE CONVERSION OF NATURAL GAS TO REACTIVE GASEOUS PRODUCTS COMPRISING ETHYLENE

(75) Inventors: Edward R. Peterson, Pearland, TX (US); Sean C. Gattis, Sugar Land, TX (US)

(73) Assignee: Synfuels International, Inc., Dallas, TX (US)

( * ) Notice: Subject to any disclaimer, the term of this patent is extended or adjusted under 35 U.S.C. 154(b) by 0 days.

(21) Appl. No.: 10/845,569

(22) Filed: May 13, 2004

(65) Prior Publication Data
US 2005/0065392 A1 Mar. 24, 2005

Related U.S. Application Data

(60) Provisional application No. 60/505,204, filed on Sep. 23, 2003.

(51) Int. Cl.
*C07C 2/78* (2006.01)

(52) U.S. Cl. .................. 585/324; 585/325; 585/540; 585/943

(58) Field of Classification Search ............... 585/324, 585/325, 540, 943
See application file for complete search history.

(56) References Cited

U.S. PATENT DOCUMENTS

| | | | |
|---|---|---|---|
| 3,389,189 A | 6/1968 | Hirayama et al. | |
| 3,663,394 A | 5/1972 | Kawahara | |
| 3,697,612 A | 10/1972 | Maniero et al. | |
| 3,703,460 A | 11/1972 | Shair et al. | |
| 3,755,488 A | 8/1973 | Johnson et al. | |
| 4,014,947 A | 3/1977 | Volodin et al. | |
| 4,134,740 A | 1/1979 | Marion et al. | |
| 4,184,322 A | 1/1980 | Paull et al. | |
| 4,256,565 A | 3/1981 | Friedman et al. | |
| 4,288,408 A | 9/1981 | Guth et al. | |
| 4,309,359 A | 1/1982 | Pinto | |
| 4,336,045 A | 6/1982 | Fisher et al. | |
| 4,513,164 A | 4/1985 | Olah | |
| 4,575,383 A | 3/1986 | Lowther et al. | |

(Continued)

OTHER PUBLICATIONS

A. Malek and S. Farooq, *Hydrogen Purification from Refinery Fuel Gas by Pressure Swing Adsorption*, AIChE Journal, Sep. 1998, vol. 44, No. 9, pp. 1985-1992.

(Continued)

*Primary Examiner*—Thuan Dinh Dang
(74) *Attorney, Agent, or Firm*—Conley Rose, P.C.

(57) ABSTRACT

A process for converting natural gas to reactive gaseous products, comprising heating the gas through a selected range of temperature for sufficient time, or combusting a portion of the gas at a sufficient temperature and under suitable conditions for a reaction time sufficient to convert a portion of the gas stream to reactive hydrocarbon products, primarily ethylene or acetylene. The gas containing acetylene may be separated such that acetylene is converted to ethylene. A portion of the incoming natural gas or hydrogen produced in the process may be used to heat the remainder of the natural gas to the selected range of temperature. Unrecovered gaseous products resulting from the reactions may be used to provide heat to the process by which reactive gas components are produced. Recovered gaseous products, together or individually, may be reserved for subsequent use or storage.

244 Claims, 13 Drawing Sheets

U.S. PATENT DOCUMENTS

| | | | |
|---|---|---|---|
| 4,704,493 A | 11/1987 | Devries et al. | |
| 4,704,496 A | 11/1987 | Paparizos et al. | |
| 4,705,906 A | 11/1987 | Brophy et al. | |
| 4,705,908 A | 11/1987 | Gondouin | |
| 4,727,207 A | 2/1988 | Paparizos et al. | |
| 4,754,091 A | 6/1988 | Jezl et al. | |
| 4,952,743 A * | 8/1990 | Come | 585/541 |
| 4,973,786 A * | 11/1990 | Karra | 585/500 |
| 5,012,028 A | 4/1991 | Gupta et al. | |
| 5,068,486 A | 11/1991 | Han et al. | |
| 5,131,993 A | 7/1992 | Suib et al. | |
| 5,254,781 A | 10/1993 | Calamur et al. | |
| 5,277,773 A | 1/1994 | Murphy | |
| 5,288,935 A | 2/1994 | Alario et al. | |
| 5,356,851 A | 10/1994 | Sarrazin et al. | |
| 5,414,170 A | 5/1995 | McCue et al. | |
| 5,749,937 A | 5/1998 | Detering et al. | |
| 5,866,056 A | 2/1999 | Werner | |
| 5,935,293 A | 8/1999 | Detering et al. | |
| 5,935,489 A | 8/1999 | Hershkowitz et al. | |
| 5,938,975 A | 8/1999 | Ennis et al. | |
| 5,981,818 A | 11/1999 | Purvis et al. | |
| 6,090,977 A | 7/2000 | Hefner et al. | |
| 6,130,260 A | 10/2000 | Hall et al. | |
| 6,187,226 B1 | 2/2001 | Detering et al. | |
| 6,323,247 B1 | 11/2001 | Hall et al. | |
| 6,358,399 B1 | 3/2002 | Minkkinen et al. | |
| 6,365,790 B2 | 4/2002 | Reimer et al. | |
| 6,365,792 B1 | 4/2002 | Stapf et al. | |
| RE37,853 E | 9/2002 | Detering et al. | |
| 6,518,476 B1 | 2/2003 | Culp et al. | |
| 6,566,573 B1 | 5/2003 | Bharadwaj et al. | |
| 6,596,912 B1 | 7/2003 | Lunsford et al. | |
| 6,602,920 B2 | 8/2003 | Hall et al. | |
| 2002/0000085 A1 * | 1/2002 | Hall et al. | 60/39.02 |
| 2002/0068843 A1 | 6/2002 | Dai et al. | |
| 2003/0021746 A1 | 1/2003 | Fincke et al. | |
| 2004/0002553 A1 | 1/2004 | Hall et al. | |

OTHER PUBLICATIONS

International Search Report, PCT/US03/38871, Date of Mailing Dec. 6, 2004.

* cited by examiner

PROCESS FOR THE CONVERSION OF NATURAL GAS TO REACTIVE GASEOUS PRODUCTS COMPRISING ETHYLENE

CROSS-REFERENCE TO RELATED APPLICATIONS

The present application claims the benefit of 35 U.S.C. 111(b) U.S. provisional application Ser. No. 60/505,204 filed Sep. 23, 2003, and entitled Process For The Conversion of Natural Gas To Hydrocarbon Liquids And Ethylene.

STATEMENT REGARDING FEDERALLY SPONSORED RESEARCH OR DEVELOPMENT

Not Applicable.

BACKGROUND OF THE INVENTION

1. Field of the Invention

This invention relates to processes for the conversion of natural gas to reactive gaseous products. More particularly, this invention relates to processes for the conversion of natural gas to reactive gaseous products wherein natural gas is first converted to gaseous reactive hydrocarbon products and gaseous co-products and the reactive hydrocarbon products are then reacted further to produce final products initially comprising ethylene.

2. Description of the Related Art

Natural gas typically contains about 60–100 mole percent methane, the balance being primarily heavier alkanes. Alkanes of increasing carbon number are normally present in decreasing amounts. Carbon dioxide, hydrogen sulfide, nitrogen, and other gases may be present in relatively low concentrations.

The conversion of natural gas into valuable reactive hydrocarbon and reactive non-hydrocarbon products has been a technological goal for many years. This goal has become even more important in recent years as more natural gas has been found in remote locations, where gas pipelines cannot be economically justified. A significant portion of the world reserves of natural gas occurs in such remote regions. While liquefied natural gas (LNG) and methanol projects have long attracted attention by making possible the conversion of natural gas to a liquid, in recent years the advent of large-scale projects based upon Fisher-Tropsch (F-T) technology have attracted more attention. A review of proposed and existing F-T projects along with a discussion of the economics of the projects has recently been published (Oil and Gas J., Sep. 21 and Sep. 28, 1998). In this technology, natural gas is first converted to "syngas," which is a mixture of carbon monoxide and hydrogen, and the syngas is then converted to liquid paraffinic and olefinic hydrocarbons of varying chain lengths.

The conversion of natural gas to unsaturated hydrocarbons and hydrogen by subjecting the hydrocarbons in natural gas to high temperatures produced by electromagnetic radiation or electrical discharges has been extensively studied. U.S. Pat. No. 5,277,773 (Exxon Research & Eng. Co.) discloses a conversion process that treats methane and hydrocarbons with microwave radiation so as to produce an electric discharge in an electromagnetic field. U.S. Pat. No. 5,131,993 (The Univ. of Conn.) discloses a method for cracking a hydrocarbon material in the presence of microwave discharge plasma and a carrier gas, such as oxygen, hydrogen, and nitrogen and, generally, a catalyst. Expired U.S. Pat. No. 3,389,189 (Westinghouse Electric Corp.) is an example relating to the production of acetylene by an electric arc.

The traditional methods of converting lower molecular weight carbon-containing molecules to higher molecular weights are numerous. There are many patents that teach reactor designs with the purpose of converting hydrocarbon containing gases to ethylene, acetylene, or syngas. The most prevalent methods involve oxidative coupling, partial oxidation, or pyrolysis. Each method has its own benefits and its own challenges.

Oxidative coupling is a technique wherein a lighter hydrocarbon is passed through a reaction bed containing a catalyst that encourages partial oxidation of the hydrocarbon. The primary advantage of oxidative coupling is that relatively mild conditions of temperature and pressure are required. The distinguishing disadvantage of oxidative coupling is the necessity for a solid phase catalyst, which has a short useful life and must be regenerated often. U.S. Pat. No. 4,704,493 (Chevron Corp.) discloses the use of Group IIA metal oxides on various supports to convert methane into light aromatic compounds and light hydrocarbons. Although methane conversions of up to 40% are reported, there is a strong correlation between increased conversion and increased tar and coke production. U.S. Pat. No. 4,705,908 (Gondouin) teaches the conversion of natural gas containing components of $C_1$ through $C_4$–$C_{5+}$ hydrocarbons and hydrogen by first splitting the stream of natural gas into a $C_1$–$C_2$ portion and a heavier portion, and then reacting these streams separately using a single non-silica based catalyst that includes mixed oxides. The reactions are performed at different temperatures and residence times. Disadvantages of this process include expected low conversion, excessive recycling of gases, continuous movement, and regeneration of the solid catalyst. U.S. Pat. No. 5,012,028 (The Standard Oil Co.) presents a process whereby natural gas is separated into methane and $C_{2+}$ hydrocarbons and other gases, and the methane is introduced along with oxygen to a reactor operated to perform oxidative coupling. The products of oxidative coupling are then combined with the other gases and non-methane hydrocarbons in a pyrolysis reactor. A quench step and a product recovery step follow. U.S. Pat. No. 5,288,935 (Institut Francais du Petrole) teaches separating natural gas into methane and other gases rich in $C_{2+}$. The methane is subjected to oxidative coupling. The $C_{2+}$ fraction is fed to the reactor before all of the oxygen is consumed. U.S. Pat. No. 6,518,476 (Union Carbide Chem. & Plas. Tech. Corp.) teaches effective oxidative dehydrogenation of natural gas at elevated pressure, generally between 50 psi and 400 psi (about 340–2800 kPa) and below 600° C., using a rare earth oxycarbonate catalyst. The olefin yield is increased through recycling of the non-olefin containing product. The olefin is removed using silver ion-containing complexation agents or solutions. Conversions are generally on the order of 20% but can be as high as 40%, depending upon the method of operation of the reactor. Selectivity declines with increased conversion. U.S. Pat. No. 6,566,573 (Dow Global Tech., Inc.) teaches conversion of paraffinic hydrocarbons with two or more carbon atoms to olefins in the presence of oxygen, hydrogen, and a supported platinum catalyst. It is recognized that preheating of the feedstreams reduces the required flow of oxygen, with a resulting reduction in oxygen-containing byproducts such as CO and $CO_2$. Conversion of ethane to ethylene is about 55%, while acetylene production is less than 1%.

Non-catalytic partial oxidation is widely practiced because the technique is simpler as there is no catalyst to regenerate. Products generally include only gas phase components, which will generally include ethylene, carbon monoxide, carbon dioxide, and acetylene. There are many reactor designs and methods for partial oxidation. U.S. Pat. No. 4,575,383 (Atlantic Richfield Co.) discloses a unique reactor design, namely a reciprocating piston engine. Conversion of methane to ethylene and acetylene is less than 1% however, which is very low. U.S. Pat. No. 5,068,486 (Mobil Oil Corp.) reveals a partial oxidation process that operates at very high pressure (20–100 atm), necessitating very high compression costs. The conversion of methane, which is the hydrocarbon feed, is reported as 12.6%, with hydrocarbon selectivity of 32%. The overall conversion of methane to ethylene, acetylene, and propane were 1.4%, 0.4% and 0.1%, respectively. U.S. Pat. Nos. 5,886,056 and 5,935,489 (Exxon Res. and Eng. Co.) teach a multi-nozzle design for feeding a partial oxidation reactor. The multiple nozzles allow introduction of a pre-mix of oxidant and fuel at the burner face so that these gases are premixed and of uniform composition. Alternatively, the plurality of injection nozzles allows one to feed different pre-mix compositions to the partial oxidation reactor burner face, for example allowing one nozzle to act as a pilot due to a higher than average oxygen feed concentration, and those nozzles on the periphery to have a greater hydrocarbon concentration resulting in a lower temperature. A major disadvantage of such a design is that the control and operation of multiple feeds increases the probability of failure or shutdown of the reactor and also increases the cost of building the reactor. U.S. Pat. No. 6,365,792 (BASF AG) teaches that operation of a partial oxidation cracker at less than 1400° C. but for longer residence times provides similar acetylene conversion but at reduced energy costs and with less solid carbon being formed.

Pyrolysis of hydrocarbons generally requires higher temperatures than the other techniques because there are normally no oxidative or catalytic species present to facilitate dehydrogenation of the hydrocarbon. As in oxidation processes, the products are generally limited to gas phase components.

There are many ways to propagate pyrolysis reactions and some are described here. Expired U.S. Pat. No. 3,663,394 (The Dow Chem. Co.) claims use of a microwave generated plasma for converting methane and ethane to acetylene. Although conversions ranged up to 98% with about 50% acetylene being formed, the process performed best at pressures below 40 torr and especially at 10 torr, which would be difficult to achieve economically at industrial scale. Expired U.S. Pat. No. 3,697,612 (Westinghouse Elec. Corp.) describes an arc heater of complex design that can convert methane to higher hydrocarbons, wherein the conversion is about 40%. Of the total converted, acetylene accounted for 74% of the product. The energy required to create a pound of acetylene was more than 5 kilowatts, which is comparable to other methods for making acetylene using electrical discharge. Expired U.S. Pat. No. 3,703,460 (U.S. Atomic Energy Commission) teaches that ethylene and ethane can be made in an induced electric discharge plasma reactor. The process operates at atmospheric pressure or below and provides less than 6% conversion of the feed methane. A disadvantage of the process is the need for vacuum pumps, which are expensive to operate. U.S. Pat. No. 4,256,565 (Rockwell Int'l. Corp.) discloses a method to produce high yields of olefins from heavy hydrocarbon feedstock by commingling a stream of hot hydrogen and water vapor with a spray of liquefied heavy hydrocarbon consisting preferentially of asphalts and heavy gas oils. Yields of olefins are strongly dependent upon rapid heating and then cooling of the fine spray droplets, to initiate and then quench the reactions. U.S. Pat. No. 4,288,408 (L.A. Daly Co.) teaches that for cracking of heavy hydrocarbons, which tend to coke heavily, injection of an inert gas such as nitrogen or $CO_2$ just downstream of the liquid feed atomizers will decrease accumulation and formation of coke on the walls of the reactor and downstream in the gas cooler. U.S. Pat. No. 4,704,496 (The Standard Oil Co.) relates to the use of nitrogen and sulfur oxides as reaction initiators for pyrolysis of light hydrocarbons in reactors such as tubular heaters. Conversion of methane is reportedly as high as 18.5%, with selectivity to liquids as high as 57.8%, and selectivity to acetylene as high as 18.7%. U.S. Pat. No. 4,727,207 (Standard Oil Co.) teaches that the addition of minor amounts of carbon dioxide to methane or natural gas will assist in the conversion of the methane or natural gas to higher molecular weight hydrocarbons as well as reduce the amount of tars and coke formed. The examples were run at 600° C., which is a relatively low temperature for pyrolysis of methane, and the reported conversions were generally low (about 20% or less). A drawback of this technique is that the addition of $CO_2$ adds another component that must then be removed from the product, which increases both gas scrubbing costs and transmission equipment size.

U.S. Pat. No. 5,749,937 (Lockheed Idaho Tech. Co.) discloses that acetylene can be made from methane using a hydrogen torch with a rapid quench, with conversions of methane to acetylene reportedly 70% to 85% and the balance being carbon black. U.S. Pat. No. 5,938,975 (Ennis et al.) discloses the use of a rocket engine of variable length for pyrolysis of various feeds including hydrocarbons. Various combinations of turbines are disclosed for generating power and compressing gas, purportedly allowing a wide range of operating conditions, including pressure. An obvious drawback of such a rocket powered series of reactors is the complexity of the resulting design. U.S. Patent No. Application Publication No. 20030021746, U.S. Patent Nos. RE37,853E and 6,187,226 (Bechtel BWXT Id., LLC), and U.S. Pat. No. 5,935,293 (Lockheed Martin Idaho Tech. Co.) all teach a method to make essentially pure acetylene from methane via a plasma torch fueled by hydrogen. The disclosed design employs very short residence times, very high temperatures, and rapid expansion through specially designed nozzles to cool and quench the acetylene production reaction before carbon particles are produced. The disclosed technique purportedly enables non-equilibrium operation, or kinetic control, of the reactor such that up to 70% to 85% of the product is acetylene. Approximately 10% of the product is carbon. A drawback of this process is that high purity hydrogen feed is required to generate the plasma used for heating the hydrocarbon stream.

Interesting combinations of processes have also been developed. For example, U.S. Pat. No. 4,134,740 (Texaco Inc.) uses carbon recovered from the non-catalytic partial oxidation reaction of naphtha as a fuel component. A complex carbon recovery process is described wherein the reactor effluent is washed and cooled with water, the carbon is extracted with liquid hydrocarbon and stripped with steam, and then added to an oil to form a slurry that is fed back to the partial oxidation reactor. This process does not appear to be applicable to the partial oxidation of gas-phase hydrocarbons, however. The handling and conveying of slurries of carbon, which clogs pipes and nozzles, is a further drawback. U.S. Pat. No. 4,184,322 (Texaco Inc.) discusses methods for power recovery from the outlet stream of a partial oxidation cracker. The methods suggested include: 1) heat recovery steam generation with the high temperature effluent gas, 2) driving turbines with the effluent gas to create power, 3) directly or indirectly preheating the partial oxidation reactor feeds using the heat of the effluent, and 4) generating steam in the partial oxidation gas generator to operate compressors. Integration of these methods can be difficult in practice. For example, when preheating feed streams depends on the downstream temperature and effluent composition, there will be periods when the operation is non-constant and the product composition is not stable. However, no external devices are disclosed to assist in the start-up or trim of the operation to achieve or maintain stable operation and product quality. U.S. Pat. No. 4,513,164 (Olah) discloses a process combining thermal cracking with chemical condensation, wherein methane is first cracked to form acetylene or ethylene, which is then reacted with more methane over a superacid catalyst, such as tantalum pentafluoride. Products are said to consist principally of liquid alkanes. U.S. Pat. No. 4,754,091 (Amoco Corp.) combines oxidative coupling of methane to form ethane and ethylene with catalytic aromatization of the ethylene. The ethane formed and some unreacted methane is recycled to the reactor. Recycle of the complete methane stream did not provide the best results. The preferred lead oxide catalyst achieved its best selectivity with a silica support, and its best activity with an alpha alumina support. Residual unsaturated compounds in the recycle gas were said to be deleterious in the oxidative coupling reaction. It is also taught that certain acid catalysts were able to remove ethylene and higher unsaturates from a dilute methane stream, without oligomerization, under conditions of low pressure and concentration.

U.S. Pat. No. 5,012,028 (The Standard Oil Co.) teaches the combination of oxidative coupling and pyrolysis to reduce external energy input. Oxidative coupling is used to form an intermediate, principally ethylene and ethane, which is an exothermic process. The product of the oxidative coupling reaction is converted to heavier hydrocarbons, which is endothermic, in a pyrolysis reactor. Pyrolysis of $C_{2+}$ hydrocarbons to liquids does not require as high a temperature as does the pyrolysis of methane, therefore the required energy input is reduced. Because both process steps occur at temperatures below 1200° C., equipment can be readily designed to transfer heat between the processes for heat integration. A major drawback of this combination of technologies however, is controlling the composition of the intermediate because residence times are less than ½ second in both systems. Feed or control fluctuations could easily result in loss of operation and heat transfer between the units. If the units are closely coupled, such a loss of heat transfer could easily result in reactor damage. U.S. Pat. No. 5,254,781 (Amoco Corp.) discloses oxidative coupling and subsequent cracking, wherein the oxygen is obtained cryogenically from air and the products, principally $C_2$'s and $C_3$'s, are liquefied cryogenically. Effective heat integration between the exothermic oxidative coupling process step and the endothermic cracking process step is also said to be obtained. U.S. Pat. No. 6,090,977 (BASF AG) uses a hydrocarbon diluent, such as methane, to control the reaction of a different, more easily oxidized hydrocarbon, such as propylene. The more easily oxidized hydrocarbon is converted by heterogeneously catalyzed gas phase partial oxidation. After the partial oxidation reaction, combustion of the effluent gas is used to generate heat. An advantage of a hydrocarbon diluent is that it can absorb excess free radicals and thereby prevent run-away reaction conditions caused by the presence of excess oxygen. The hydrocarbon also increases the heating value of the waste gas, thus its value as a fuel. Of course, this technique cannot be utilized when the reaction conditions are such that methane reacts and/or is the predominant reactant. U.S. Pat. No. 6,596,912 (The Texas A&M Univ. System) employs a recycle system with a high recycle ratio of (8.6:1) to achieve a high conversion of methane to $C_4$ and heavier products. The initial process employs an oxidative coupling catalyst to produce primarily ethylene, and a subsequent process step using an acid catalyst such as ZSM-5 to oligomerize the ethylene. A drawback of this relatively high recycle ratio is that larger compressors and reactors are required to produce the final product.

Following cracking, some unsaturated compounds are desirably converted to hydrogenated species. The hydrogenation of unsaturated compounds is known in the art. For example, U.S. Pat. No. 5,981,818 (Stone & Webster Eng. Corp.) teaches the production of olefin feedstocks, including ethylene and propylene, from cracked gases. U.S. Pat. No. 5,414,170 (Stone & Webster Eng. Corp.) discloses a mixed-phase hydrogenation process at very high pressure. A drawback of this technique is that the concentration of acetylene must be low to enable the proper control of temperature in the hydrogenation step. U.S. Pat. No. 4,705,906 (The British Petroleum Co.) teaches hydrogenation of acetylene to form ethylene in the gas phase using a zinc oxide or sulphide catalyst. Conversions up to 100% and selectivities to ethylene up to 79% were reported.

Separation of the products of cracking is often desirable when a specific component has particular value. For example, separation of acetylene from ethylene is beneficial when the ethylene is to be used in making polyethylene. U.S. Pat. No. 4,336,045 (Union Carbide Corp.) proposes the use of liquid hydrocarbons to separate acetylene from ethylene, using a light hydrocarbon at temperatures of below −70° C. and elevated pressure.

The cogeneration of electrical power can substantially improve the economics of cracking processes. For example, U.S. Pat. No. 4,309,359 (Imperial Chem. Ind. Ltd.) describes the use of a catalyst to convert a gas stream containing hydrogen and carbon monoxide to methanol, whereby some of the gas is used to create energy via reaction in a fuel cell.

Chemical production prior to the complete separation of the products of the cracking reaction can also be used to reduce the cost of purification. U.S. Pat. No. 4,014,947 (Volodin et al.) describes a process for the pyrolysis of hydrogen and methane with conversion of the produced acetylene and ethylene to vinyl chloride. The acetylene and ethylene are reacted with chlorine or hydrogen chloride, during the pyrolysis formation of the unsaturated hydrocarbons, and rapidly quenched with a liquid hydrocarbon.

U.S. Pat. Nos. 6,130,260 and 6,602,920 (The Texas A&M Univ. Systems) and U.S. Pat. No. 6,323,247 (Hall et al) describe a method in which methane is converted to hydrogen and acetylene at temperature, quenched, and catalytically converted to, inter alia, pentane. While an advance over conventional art processes, the method disclosed still suffers from a number of drawbacks with respect to the preferred embodiments of the process of the present invention, as will be further described herein. In particular, the production and integration of carbon monoxide and carbon dioxide within the process is not contemplated by the reference. Carbon monoxide is produced in preferred embodiments of the present invention that include a partial oxidation step, and it provides additional value to the inventive processes as both a downstream feedstock and a fuel. Carbon dioxide that can be used to reduce the carbon formation in process equipment and increase the overall process yield is also produced in preferred embodiments of the present invention that include direct heating.

Further advantages are provided by the employment of the various separation processes described in preferred embodiments of the present invention. For example, preferred embodiments of the present invention provide for the separation of acetylene from other gas components prior to hydrogenation, with corresponding reductions in the quantity of gas that must be treated in the hydrogenation steps. Improvements in catalyst life may also be expected therefrom. Ethylene management in accordance with preferred embodiments of the present invention provides additional advantages, as illustrated by inventive preferred embodiments comprising removal of ethylene from acetylene-deprived streams, with their subsequent combination with ethylene-rich hydrogenator product streams. In some preferred embodiments of the present invention, fractionation of the natural gas feed prior to conversion steps allows different reaction conditions for the various fractions, thus improving the performance of the overall process and optimization of the product mix.

Additional advantages are provided by the unit operations uniquely employed in accordance with preferred embodiments of the processes of the present invention. Direct heat exchange, but one such example, is utilized to enhance conversion and reduce carbon formation in certain preferred embodiments of the present invention by placing the heating medium in direct contact with the reactant gas, thus enabling chemical reactions and equilibria that would not otherwise obtain. Similarly, the above-mentioned conventional processes do not disclose the recycle of gas components other than hydrogen to the combustor for the indirect transfer of heat, or for combination with the incoming natural gas feed stream. Preferred embodiments of the present invention however, provide for the separation of non-hydrogen components upstream and downstream of the hydrogenator with recycle for improving the acetylene yield, with the further option of recycle to the combustion stage, if the heating value of the stream provides an economic advantage.

Numerous methods for cracking hydrocarbons, particularly natural gas and methane, are known in the art. Likewise, many methods have been developed for separation of the products from cracking reactions, and many designs have been disclosed for producing ethylene and acetylene from cracking processes. However, no economical and integrated method is presently known in the art for the conversion of methane and natural gas to ethylene and other valuable final products, through the intermediate manufacture of acetylene, such that the final products can be either transported efficiently from remote areas to market areas (or used at the point of manufacture).

Although the prior art discloses a broad range of methods for forming acetylene or ethylene from natural gas, an energy-efficient process for converting natural gas to reactive gaseous products comprising ethylene has not previously been available. A way of overcoming these problems is needed so that production from natural gas of reactive gaseous products comprising ethylene is practical for commercial industrial-scale applications. Accordingly, research has focused on developing new processes that can reduce or eliminate the problems associated with the prior art methods. The processes of the present invention in their various preferred embodiments are believed to both overcome the drawbacks of the prior art and provide a substantial advancement in the art relating to the conversion of natural gas to ethylene containing gaseous products. The present invention has been developed with these considerations in mind and is believed to be an improvement over the methods of the prior art.

BRIEF SUMMARY OF SOME OF THE PREFERRED EMBODIMENTS

It is thus an object of the present invention to overcome the deficiencies of the prior art and thereby to provide an integrated, energy-efficient process for converting natural gas to valuable reactive gaseous products. Accordingly, provided herein is a process for the conversion of natural gas to streams substantially comprised of ethylene and hydrogen.

In some preferred embodiments, natural gas is heated to a temperature at which a fraction is converted to hydrogen and one or more reactive hydrocarbon products such as acetylene or ethylene. The product stream is then quenched to stop any further reactions. In some preferred embodiments, hydrogen may be separated after quenching. Heat for raising the temperature of the natural gas stream may preferably be provided by burning a gas recovered from downstream processing steps, or by burning a portion of the natural gas feed stream. Hydrogen produced in the reaction is preferably available for further refining, export, or in generation of electrical power, such as by oxidation in a fuel cell or turbine.

In some preferred embodiments, heat produced from a fuel cell is preferably used to generate additional electricity. In other preferred embodiments, the acetylene portion of the reactive hydrocarbon is reacted with hydrogen to form ethylene. In other preferred embodiments, some of the produced hydrogen may be burned to raise the temperature of the natural gas stream, and the acetylene portion of the reactive hydrocarbon may be reacted with more hydrogen to form ethylene.

In other preferred embodiments, hydrogen produced in the process may be used to generate electrical power, the electrical power may be used to heat the natural gas stream, and the acetylene portion of the reactive hydrocarbon stream may be reacted with hydrogen to form ethylene. In certain other preferred embodiments, acetylene may be separated from the stream containing reactive hydrocarbon products prior to subjecting the acetylene to hydrogenation, while in other preferred embodiments the stream containing acetylene is subjected to hydrogenation.

In still other preferred embodiments, the stream from which the acetylene has been removed is subjected to further separation such that ethylene is removed, making this ethylene available for combination with the acetylene. In other preferred embodiments, the ethylene stream and the product of the acetylene hydrogenation step may be combined.

In another preferred embodiment, either separate or combined ethylene streams may be separated for further processing. In certain other preferred embodiments, the heating of one portion of the natural gas feed is accomplished by the complete combustion of a second portion of the natural gas, which is accomplished within a reactive structure that combines the combusted natural gas and natural gas to be heated.

In other preferred embodiments, the heating of a portion of the natural gas is accomplished by mixing with an oxidizing material, such that the resulting incomplete combustion produces heat and the reaction products may comprise reactive hydrocarbon products.

In other preferred embodiments, the carbon monoxide that is produced by the incomplete combustion of natural gas or other hydrocarbons is recycled to a section or sections of the reactor as a fuel component. In yet other preferred embodiments, the carbon monoxide that is produced by the incomplete combustion of the natural gas feed or other hydrocarbons is used in subsequent chemical processing. In another preferred embodiment, hydrogen that is produced in the reactor is separated from the reactive components and then used in subsequent chemical processing.

In another preferred embodiment, hydrogen and carbon monoxide produced in the process are subsequently combined to form methanol.

DETAILED DESCRIPTION OF THE PREFERRED EMBODIMENTS

Herein will be described in detail specific preferred embodiments of the present invention, with the understanding that the present disclosure is to be considered an exemplification of the principles of the invention, and is not intended to limit the invention to that illustrated and described herein. The present invention is susceptible to preferred embodiments of different forms or order and should not be interpreted to be limited to the specifically expressed methods or compositions contained herein. In particular, various preferred embodiments of the present invention provide a number of different configurations of the overall gas to liquid conversion process.

Figure 1:
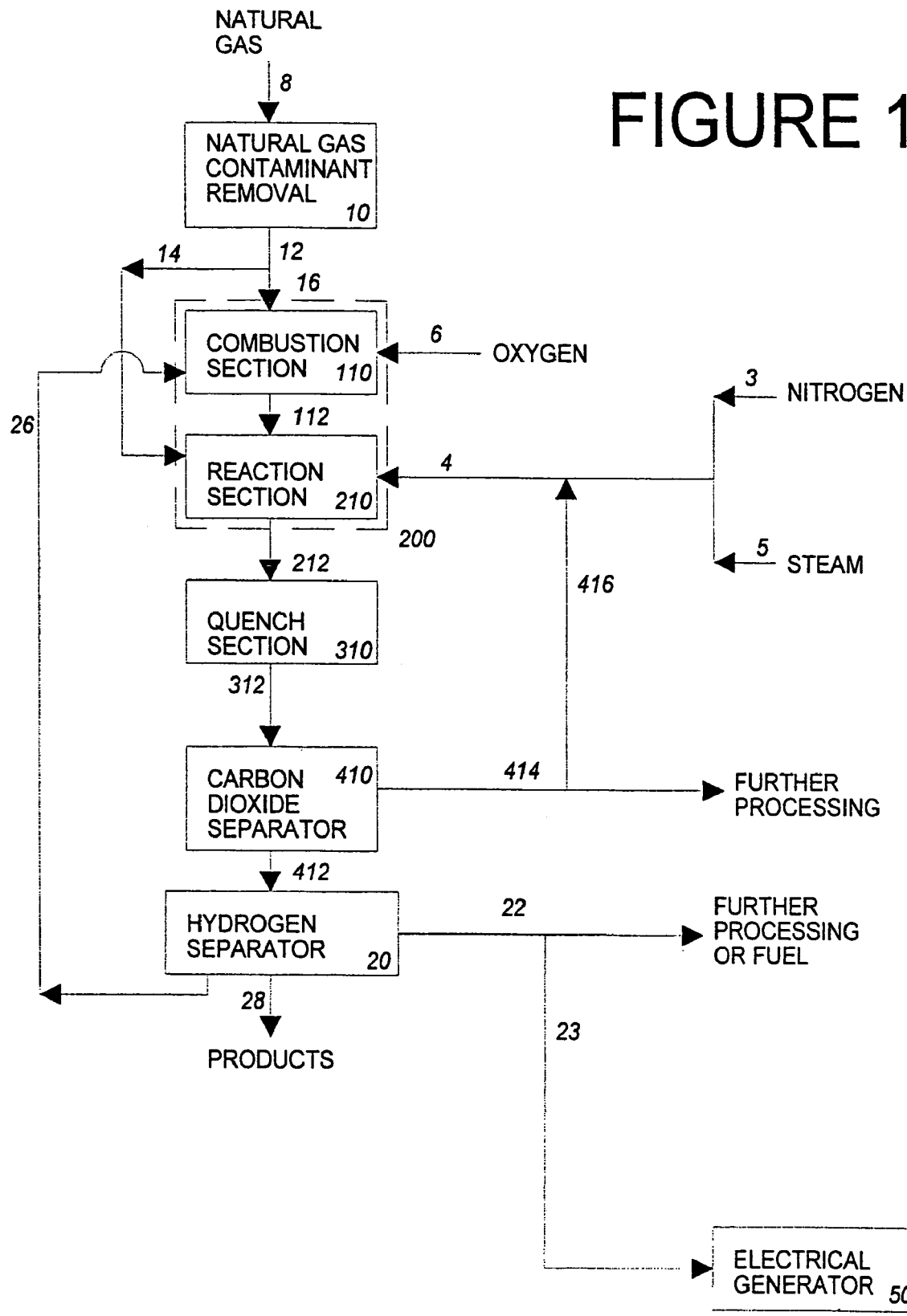
FIG. 1 is a schematic process flow diagram illustrating preferred embodiments of the process of the present invention in which a first portion of the natural gas is heated to reaction temperature by essentially complete combustion of a second portion of the natural gas upstream, with subsequent mixing of the streams to convey heat from the second stream to the first stream in a mixed stream reactor.

Referring now to FIG. 1, shown therein are certain preferred embodiments for producing a reactive product such as ethylene from natural gas in accordance with the present invention. In these preferred embodiments, impurities and contaminants may be first removed from the inlet natural gas stream. Thereafter, a portion of the natural gas feed is diverted from the feed stream to a burner, which may preferably be an in-line upstream burner, where the diverted natural gas is burned, preferably with oxygen enriched air such that $NO_x$ production from the combustion section of the reactor is minimized. As shown in FIG. 1, produced gas stream 8 may be first cleaned of contaminants in natural gas contaminant removal 10 to produce clean gas stream 12. Clean gas stream 12 may preferably be separated into inlet gas feed stream 14 and inlet gas burn stream 16. Inlet gas feed stream 14 is conveyed to the reaction section 210 of the reactor 200. Inlet gas burn stream 16 is conveyed to the combustion section 110 of the reactor 200. Oxygen or oxygen-containing gas is provided to combustion section 110 via oxygen line 6. Nitrogen via nitrogen line 3 and/or steam via steam line 5 preferably may also be provided to reaction section 210 via inlet stream 4. Inlet gas feed stream 14 is preferably pre-heated in pre-heaters (not shown) before it is heated to the preferred reaction temperature by direct heat exchange through combination with the hydrocarbon-combustion gas. The flame temperature of inlet gas burn stream 16 is preferably adequate to reach a desired reaction temperature preferably between 1000° and 2800° K with air or oxygen or a combination of air and oxygen. The addition of water or steam (not shown) to the combustion section 110 of the reactor may be used to lower and thereby control the combustion gas temperature. The residence time of the combined combustion and feed gas in the reaction section 210 of the reactor should be sufficient to convert inlet gas feed stream 14 to acetylene, ethylene, and other reactive compounds, and not so long as to allow significant further reactions to occur before quenching, which is discussed below. It is preferred to maintain the residence time to under 100 milliseconds and, more preferably, under 80 milliseconds, to minimize coke formation. Residence times in excess of 0.1 milliseconds and more desirably 0.5 milliseconds are preferred to obtain sufficient conversion. The desired products from this series of reactions are ethylene and acetylene and most preferably acetylene.

Suppression of the production of other components may be required to achieve the desired reactive products. This may be accomplished by such methods as adjusting the reaction temperature, pressure, or both, quenching after a desired residence time. It is preferred to maintain the pressure of the natural gas within the reaction section 210 of the reactor 200 to between 1 and 20 bar (100–2000 kPa) to achieve the preferred reactive products. The reactive products resulting from reaction in reaction section 210 of the reactor leave with the combustion products and any unconverted feed through the reaction section outlet stream 212. The desired reactive products of the reactions are designated herein as "reactive hydrocarbon products."

The temperature rise in the feed, combustion, or combined gas should preferably occur in a short period of time. The reactor 200 may preferably be designed to accommodate one or more natural gas feed streams, which may employ natural gas combined with other gas components including, but not limited to: hydrogen, carbon monoxide, carbon dioxide, ethane, and ethylene. The reactor 200 may preferably have one or more oxidant feed streams, such as an oxygen stream and an oxygen-containing stream such as an air stream, which employ unequal oxidant concentrations for purposes of temperature or composition control. As is well known to those skilled in the art, Reactor 200 may comprise a single device or multiple devices. Each device may comprise one or more sections. In the example shown in FIG. 1, products from combustion section 110 go to reaction section 210 schematically as stream 112. Depending on the type and configuration of reactor 200 used, stream 112 may not be isolatable.

To stop the desired reactions taking place in reaction section 210, prevent the reverse reactions, or prevent further reactions to form carbon and other hydrocarbon compounds, rapid cooling or "quenching" is preferred in quench 310, and it is more preferred that quenching take place within about 1 to 100 milliseconds. As shown in, for example, FIG. 1, reaction section outlet stream 212 is directed to quench section 310 where it is quenched before exiting through quench outlet stream 312. The quench section 310 preferably achieves quenching of reaction section outlet stream 212 by any of the methods known in the art including, without limitation, spraying a quench fluid such as steam, water, oil, or liquid product into a reactor quench chamber; conveying through or into water, natural gas feed, or liquid products; preheating other streams such as 6, 12, or 14 of FIG. 1; generating steam; or expanding in a kinetic energy quench, such as a Joule Thompson expander, choke nozzle, or turbo expander. Use of certain quench fluids may induce further chemical reactions to occur, possibly creating additional reactive hydrocarbon products, thereby increasing the overall energy and economic efficiency of the process, particularly when recovered or recycled streams from downstream processing steps are used as the quench fluids. Quenching can be accomplished in multiple steps using different means, fluids, or both. Accordingly, quench section 310 may be incorporated within reactor 200, may comprise a separate vessel or device from reactor 200, or both.

Referring again to FIG. 1, it is to be noted that "lean" natural gas, i.e., gas with 95% or greater methane, reacts to mostly acetylene as a reactive product. Where the produced natural gas stream 8 is lean, it is preferred to operate the reaction section 210 in the upper end of the available temperature range to achieve a higher content of alkynes in the product, in particular acetylene. In contrast, with a richer natural gas stream, it may be preferable to operate reaction section 210 at a temperature lower in the desirable range to achieve a higher content of alkenes in the product, primarily ethylene.

In certain preferred embodiments illustrated in FIG. 1, a portion of the product of hydrogen separator 20 represented by stream 26 may be recycled and burned in the combustion section 110 of reactor 200. Stream 22 comprising hydrogen from hydrogen separator 20 may be used in any number of processes (not shown) or may be burned as fuel. Hydrogen separator outlet stream 28 comprises the reactive gaseous products comprising ethylene, portions of which may be recycled, sent to storage, exported or sent to further processing, such as, for example, conversion, purification, or both. The term "reactive gaseous products" as used throughout this document is intended to designate the stream containing the final reactive products that may be removed from the process and to differentiate the stream from other intermediate streams earlier in the process that may also contain some of the same reactive components, such as, for example, ethylene. The term "gaseous", within the phrase "reactive gaseous products", identifies the physical sate of the main product constituents at standard conditions of temperature and pressure (i.e. hydrogen, ethylene). The word "gaseous" in this context is not meant to indicate the actual physical state of the stream or of its components at other process conditions. Depending upon the process conditions involved, the reactive gaseous products stream may be stored, transported through, or removed from the process as a liquid.

In other preferred embodiments, as further shown in FIG. 1, a portion of stream 22, shown as stream 23, may preferably be used in electrical generator 50, which may comprise a fuel cell or fuel cells, or any other hydrogen-fed electrical power generation device as known in the art to, for example, generate water and electricity by combination with oxygen, or by burning with oxygen in a combustion turbine. It is also within the scope of this invention that the aforementioned hydrogen can be used indirectly to generate electricity by any method known to those skilled in the art, including burning or pressure reduction, wherein the energy from burning or pressure reduction is used first to impart energy to a second substance, such as water to create steam or steam to create higher pressure steam, such that the second substance is used to generate electrical energy. The particular equipment employed in electrical generator 50 is not important to the embodiment of the invention, and any mechanism reasonably known to those skilled in the art may preferably be employed herein without departing from the scope of the invention.

The term "portion" as used throughout this document is intended to mean a variable quantity ranging from none to all (i.e. 0% to 100%) with the specific quantity being dependent upon many internal factors, such as compositions, flows, operating parameters and the like as well as on factors external to the process such as desired products and by-products, or availability and cost of electrical power, fuel, or utilities. Where "portion" is used to refer to none or 0% of a chemical component in the context of a process step, thus indicating that the process step is not performed, it should be understood to be synonymous with the term "optionally" in the context of the process step.

Figure 2:
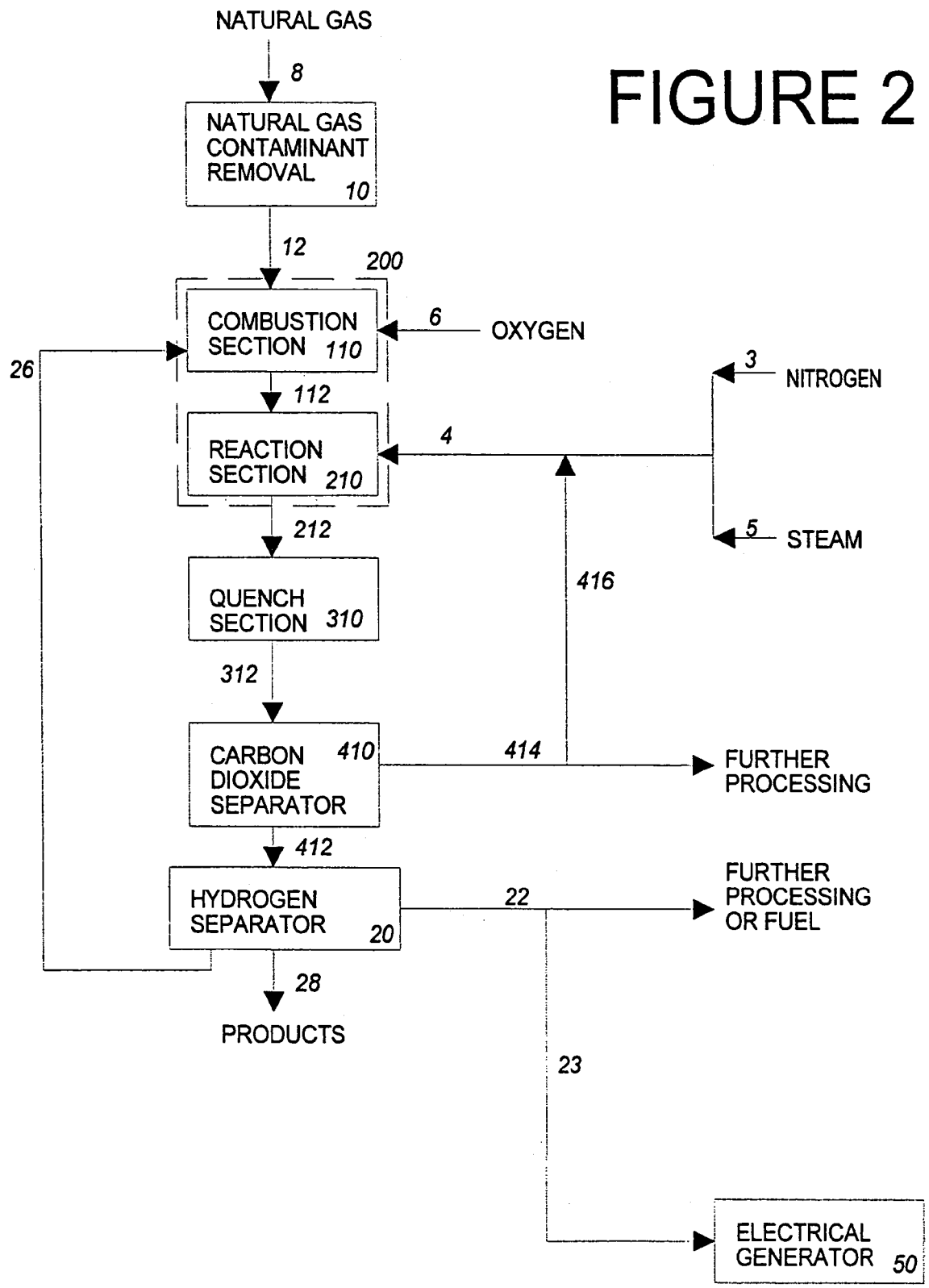
FIG. 2 is a schematic process flow diagram illustrating preferred embodiments of the process of the present invention in which the natural gas is heated to reaction temperature by incomplete combustion in a mixed stream reactor after which the reactive hydrocarbon products are separated from the non-hydrocarbons and non-reactive hydrocarbons and the reactive hydrocarbon products are subjected to hydrogenation.

In other preferred embodiments, shown in FIG. 2, feed and fuel are introduced to the reactor 200 together via inlet gas stream 12. Oxidant, insufficient for complete combustion, is introduced to the reactor 200 via stream 6, providing for incomplete combustion in combustion section 110. Reactive products, comprising the desired reactive hydrocarbon products, are then formed during and within the incomplete combustion process. The preferred products from this series of reactions comprise ethylene and acetylene, and most preferably acetylene. Suppression of the production of other components may be required to achieve the desired reactive hydrocarbon products. This may be accomplished by such methods as adjusting the reaction temperature and pressure and/or quenching after a desired residence time. Carbon dioxide may be removed from outlet stream 312 via carbon dioxide separator 410 to stream 414, by which it may be removed from the process, or a portion of stream 414 may be recycled to the reaction section 210 via stream 416 and inlet stream 4 to reduce carbon formation or improve reaction yield. Carbon dioxide may be separated from other streams or locations (not designated in FIG. 2) within the process to be either removed from the process or recycled, where such separation may be either 'in addition to' or 'in place of' carbon dioxide separator 410. As mentioned above, the desired hydrocarbon products of the reactions are designated herein as "reactive hydrocarbon products". It is preferred to maintain the pressure of the natural gas within the reaction section 210 of the reactor between 1 and 20 bar (100–2000 kPa) to achieve the reactive hydrocarbon products. The reactive hydrocarbon products resulting from reaction in reaction section 210 of the reactor 200 leave with the combustion products and any unconverted feed through the reaction section outlet stream 212.

Figure 3:
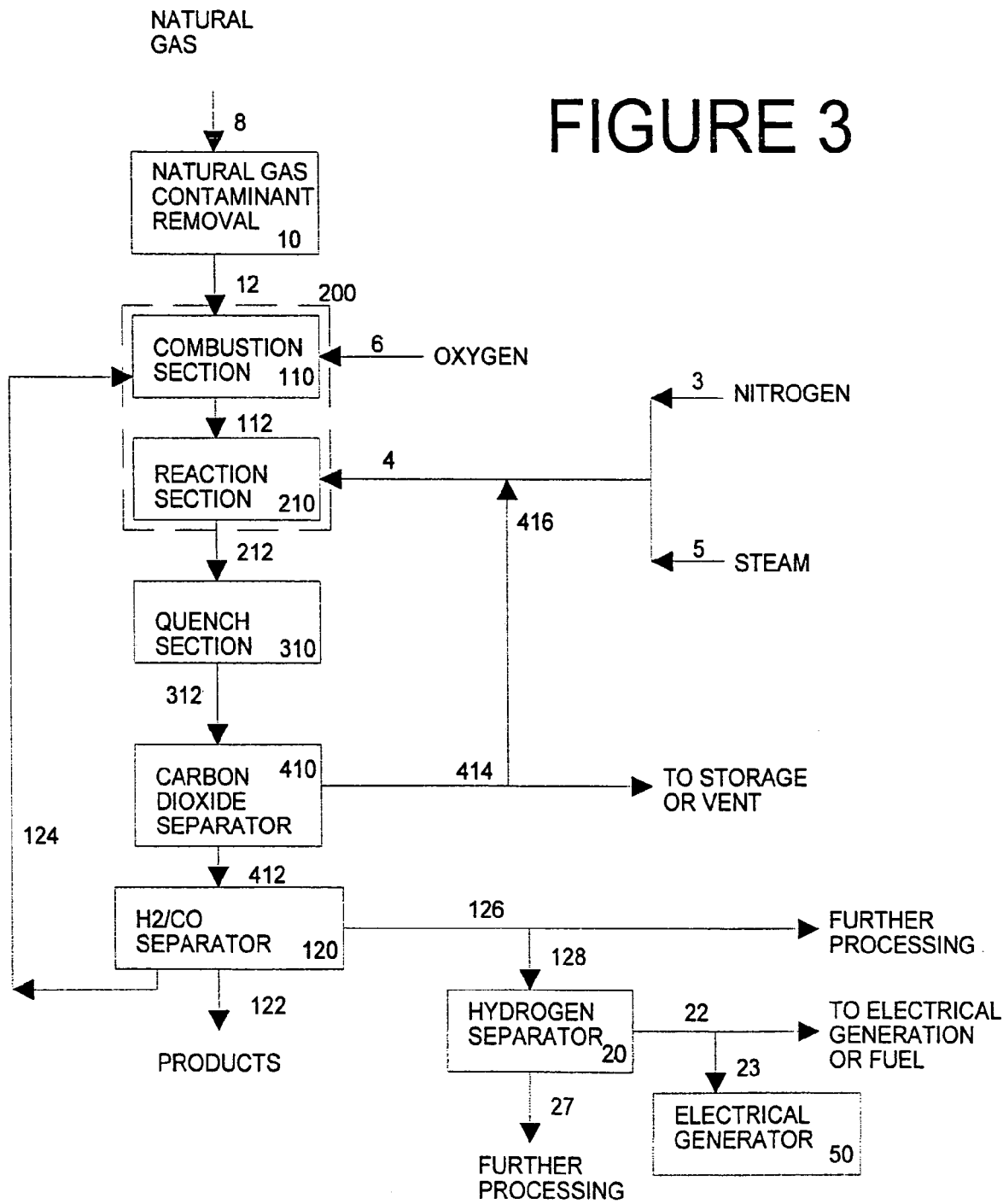
FIG. 3 is a schematic process flow diagram illustrating preferred embodiments of the process of the present invention in which the natural gas is heated to reaction temperature by burning a stream comprising natural gas and a portion of the stream comprising hydrogen and, in some cases, carbon monoxide produced with the reactive hydrocarbon products in the mixed stream reactor, after which the reactive hydrocarbon products are separated from the non-hydrocarbons and non-reactive hydrocarbons, and the reactive hydrocarbon products are subjected to hydrogenation.

In other preferred embodiments, shown in FIG. 3, natural gas in stream 12 to be burned in combustion section 110 is combined in the reactor 200 with at least hydrogen that has been produced in the reactor with the reactive hydrocarbon products and removed downstream. The hydrogen-containing stream 124 may be preferably separated from the outlet stream 412 in $H_2$/CO separator 120 by conventional means including, but not limited to, pressure swing absorption, membrane separation, cryogenic processing, and other gas separation techniques commonly practiced by those skilled in the art. When insufficient oxygen via stream 6 is introduced to combustor 110 to provide for complete combustion of either the separate stream of natural gas 12 intended as combustion gas or the combined stream of natural gas which serves as feed gas and combustion gas, carbon monoxide may be formed. If formed, this carbon monoxide may be combined in whole or in part with the hydrogen-containing stream 124 that may be separated in separator 120 and recycled to the combustion section 110. Use of carbon monoxide in this manner may supply additional energy to the combustion process that would otherwise not be available, and may preferably provide a source of control for the combustion temperature of the natural gas mixture in combustion section 110 as the combustion of carbon monoxide will, in general, deliver less energy to the combustion process than the natural gas hydrocarbon components or hydrogen, and may preferably provide a reactant that will alter and diminish the severity of reaction conditions that lead to coke formation, thus reducing coke formation. Separator 120 outlet stream 122 comprises the reactive gaseous products comprising ethylene, portions of which may be recycled, sent to storage, exported or sent to further processing, such as, for example, conversion, purification, or both. A stream comprising at least hydrogen and carbon monoxide can be taken from H2/CO separator 120 as stream 126 and sent to further processing (not shown), such as, for example, methanol production or Fisher-Tropsch reactions or units. Depending on composition, stream 126 may comprise syngas, or synthesis gas. It is well known that syngas and methanol are intermediates in the production of many different chemical and fuel production processes. A portion of stream 126 as stream 128 may be subjected to further separation in separator 20, yielding a stream 22 comprising hydrogen. Portions of stream 126, or many of their components if separated, can also be used to generate electricity, burned as fuel, flared, or vented, as can the hydrogen lean gas stream 27 from separator 20.

Figure 4:
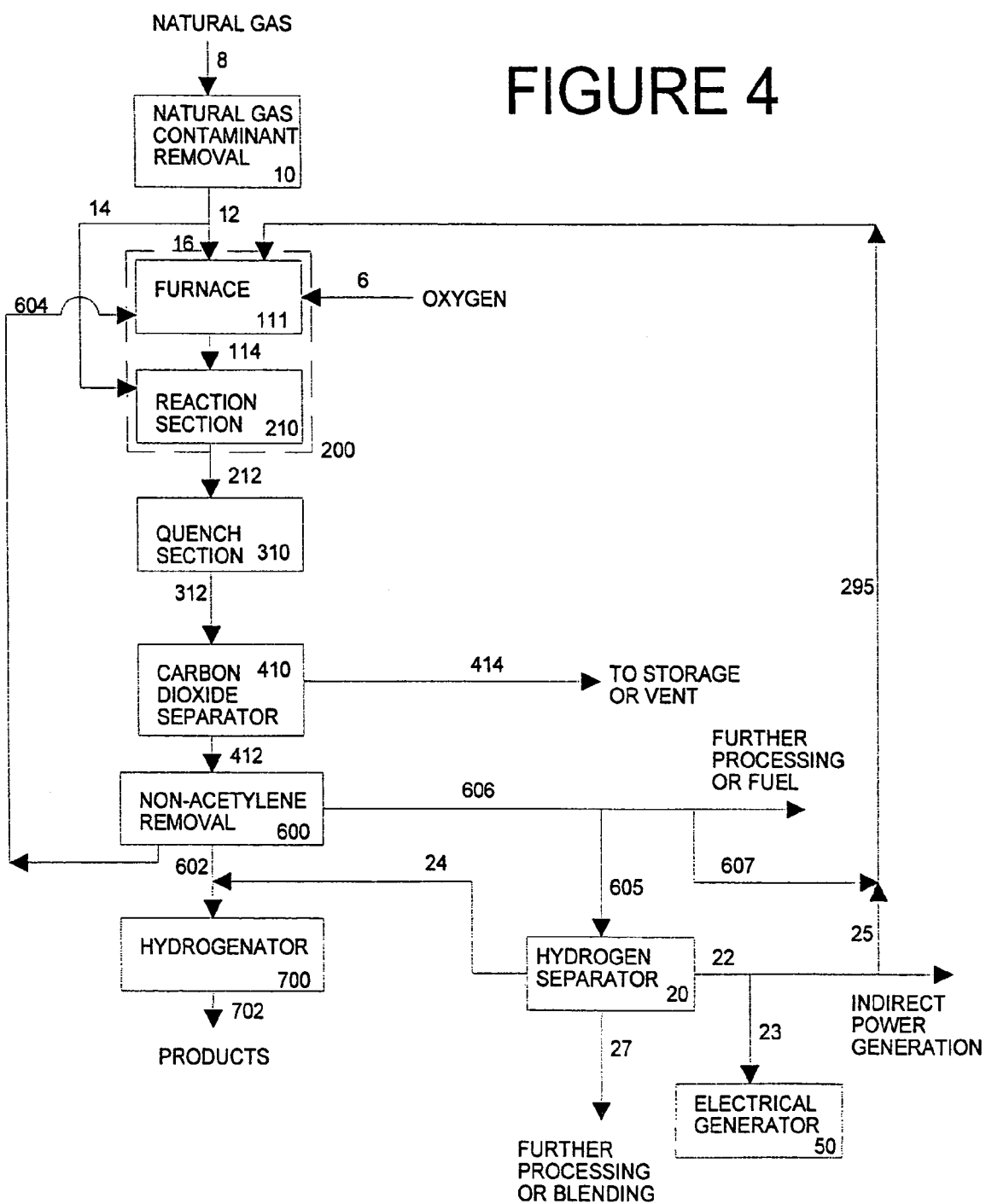
FIG. 4 is a schematic process flow diagram illustrating preferred embodiments of the process of the present invention in which the natural gas is heated to reaction temperature by a furnace. Acetylene is separated from the reaction products and hydrogenated and the remaining gas components may be vented, reserved for subsequent processing, or returned to the process to be burned or further reacted.

In other preferred embodiments, such as those shown in FIG. 4, outlet stream 114 from furnace 111 goes to reaction section 210. Depending on the configuration of reactor 200 used, stream 114 may not be isolatable. Section 210 outlet stream 212 produced by pyrolysis, and containing reactive hydrocarbon components that comprise reactive hydrocarbon products comprising acetylene and ethylene, as well as hydrogen, unreacted hydrocarbons, carbon monoxide, and carbon dioxide, is quenched in quench section 310. Carbon dioxide may be removed in carbon dioxide separator 410, and resulting stream 412 may be subjected to selective separation at non-acetylene removal 600 such that principally acetylene, the preferred reactive hydrocarbon, is separated from stream 412. The stream 602 that contains acetylene may be selectively subjected to hydrogenation in hydrogenator 700 apart from the stream 412 from which it was removed. Hydrogenator 700 outlet stream 702 comprises the reactive gaseous products comprising ethylene, portions of which may be recycled, sent to storage, exported or sent to further processing, such as, for example, conversion, purification, or both. A portion of the acetylene lean gas from non-acetylene removal 600 represented by stream 604 may be burned in furnace 111. Depending upon composition, the stream 606 from which acetylene is removed may comprise syngas, or synthesis gas, and could be, for example, used for methanol production or in Fisher-Tropsch reactions or units. Stream 606 may be returned in part or whole via stream 607 and recycle stream 295 to furnace 111 to be burned as fuel, recycled as feed, or both. A portion of stream 606 may be sent via stream 605 to separator 20. Stream 22 comprising hydrogen can be returned, in whole or in part, as streams 25 and 295 to furnace 111. A portion of the hydrogen recovered in separator 20 may be supplied to hydrogenator 700 via stream 24. A portion of stream 606 may be sent to further processing (not shown), burned as fuel, used to generate electricity, flared, or vented.

Figure 5:
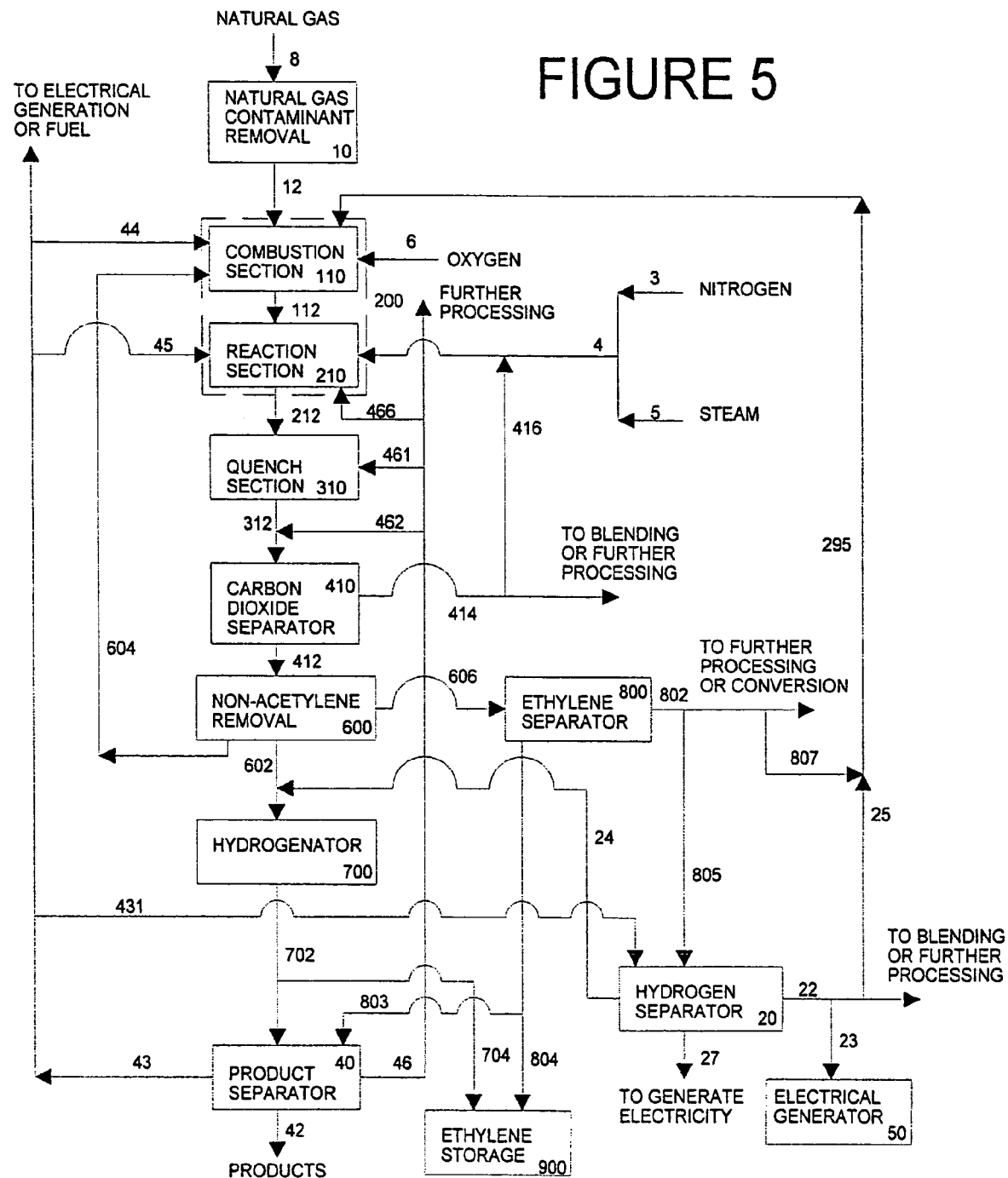
FIG. 5 is a schematic process flow diagram illustrating preferred embodiments of the process of the present invention in which the natural gas is heated to reaction temperature by incomplete combustion in a mixed-stream reactor. The reaction products containing acetylene are subjected to separation, such that the acetylene is separated from the other gas components, and the acetylene stream is then hydrogenated. The other (non-acetylene) gas components may be vented, reserved for subsequent processing or chemical conversion, or returned to the process to be burned, further reacted or, after further separation, certain components of the reaction products gas stream may be combined with the acetylene hydrogenation product stream.

In other preferred embodiments, shown in FIG. 5, the reactor outlet stream produced by partial oxidation, containing reactive hydrocarbon components, which preferably comprise reactive hydrocarbon products such as acetylene and ethylene, as well as hydrogen, unreacted hydrocarbons, carbon monoxide, carbon dioxide and, depending on the operation conditions, nitrogen, may be subjected to selective separation such that principally acetylene, the preferred reactive hydrocarbon, is separated from the remaining products at non-acetylene removal 600. This separation may be performed according to known methods such as absorption, distillation, selective membrane permeation, pressure swing absorption, or other gas separation techniques known to those skilled in the art. The stream 602 that contains acetylene may be selectively subjected to hydrogenation at hydrogenator 700 apart from the stream 412 from which it was removed. This acetylene rich stream may be wholly acetylene or combined with other gas fractions or liquid fractions used for, or to enhance, the separation process. A portion of the acetylene lean gas from non-acetylene removal 600 represented by stream 604 may be burned in combustion section 110 of reactor 200.

Referring still to FIG. 5, hydrogenator 700 outlet stream 702, which comprises the reactive gaseous products comprising ethylene, may be sent in whole or in part via stream 704 to ethylene storage 900. A portion of stream 702 may preferably be sent to product separator 40. The primary purpose of product separator 40 is to separate the desired reactive products, such as, for example, ethylene or other olefins, from any other components that may be present. Such other components may include lighter, primarily gaseous, components, such as hydrogen, carbon dioxide, carbon monoxide, nitrogen, methane, or ethane as possible examples. Such other components may include compounds with boiling points higher than that of ethylene, such as butanes, pentanes, and heavier alkanes as well as their unsaturated analogs as possible non-exclusive examples. It should be understood that an internal cooling step (not shown) may be considered a part of product separator 40. Cooling of a portion of the hydrogenation outlet stream 702 may be preferred, depending upon the method of final separation and the optimum conditions for that separation. Product separator 40 may comprise any appropriate separation methods as will be known to, and within the skill of, those practicing in the art. Distillation, adsorption or absorption separation processes, including cryogenic distillation, pressure-swing adsorption and membrane separation as a few examples, may also be used for the product separator 40. Outlet stream 42, which may be a vapor, liquid, or combination, comprises the desired reactive gaseous products, portions of which may be recycled, sent to storage, exported or sent to further processing, such as, for example, conversion, purification, or both, (not shown). A portion of the primarily gaseous components separated in product separator 40, shown as stream 43, may be sent to combustion section 110 of reactor 200 via stream 44. A portion of stream 43 may be sent via stream 45 to reaction section 210 of reactor 200. If sufficient hydrogen is present, a portion of stream 43 may be sent via stream 431 to hydrogen separator 20. Portions of stream 43 may also be burned as fuel or used for other purposes, such as electrical power generation (not shown). Vapor or liquid may be removed from product separator 40 as stream 46. Depending on its composition and quantity, portions of stream 46 may be recycled to reaction section 210 of reactor 200 via stream 466, sent to quench section 310 via stream 461 for reaction quenching or subsequent cooling, or recycled via stream 462 to the quench section 310 outlet stream 312, burned as fuel, exported, used for other purposes, such as electrical power generation (not shown), or combinations thereof.

In other preferred embodiments, shown in FIG. 5, the stream 606 that has been reduced in acetylene concentration may be subjected to gas separation techniques whereby the ethylene fraction, if in sufficient concentration, may be separated at ethylene separator 800 from the stream 802 of remaining components. If formed, this stream 804, either alone or in combination with stream 704, can be reserved at ethylene storage 900 for recycle, conversion, purification or export. If desired, streams sent to ethylene storage 900 can be subjected to liquefaction by means of a catalyst to form liquid hydrocarbons (not shown). A portion of stream 804 may be sent via stream 803 to product separator 40. Remaining components in stream 802, including but not limited to hydrogen, carbon dioxide, and carbon monoxide, and potentially unreacted hydrocarbons, nitrogen, and unseparated ethylene, as examples of components of this stream, can be recycled to reactor 200 via stream 807 and recycle stream 295. A portion of stream 802 can also be sent to further processing (not shown). Depending on composition, stream 802 may comprise syngas, or synthesis gas, and could be, for example, used for methanol production or in Fisher-Tropsch reactions or units. It is well known that syngas and methanol are intermediates in the production of many different chemical and fuel production processes. Stream 802 can also be subjected to further separation, in some cases yielding a hydrogen stream, such as, for example, when a portion is sent via stream 805 to hydrogen separator 20. Stream 802, or streams separated from stream 802, can also be burned as fuel, used to generate electricity, flared, or vented.

Figure 6:
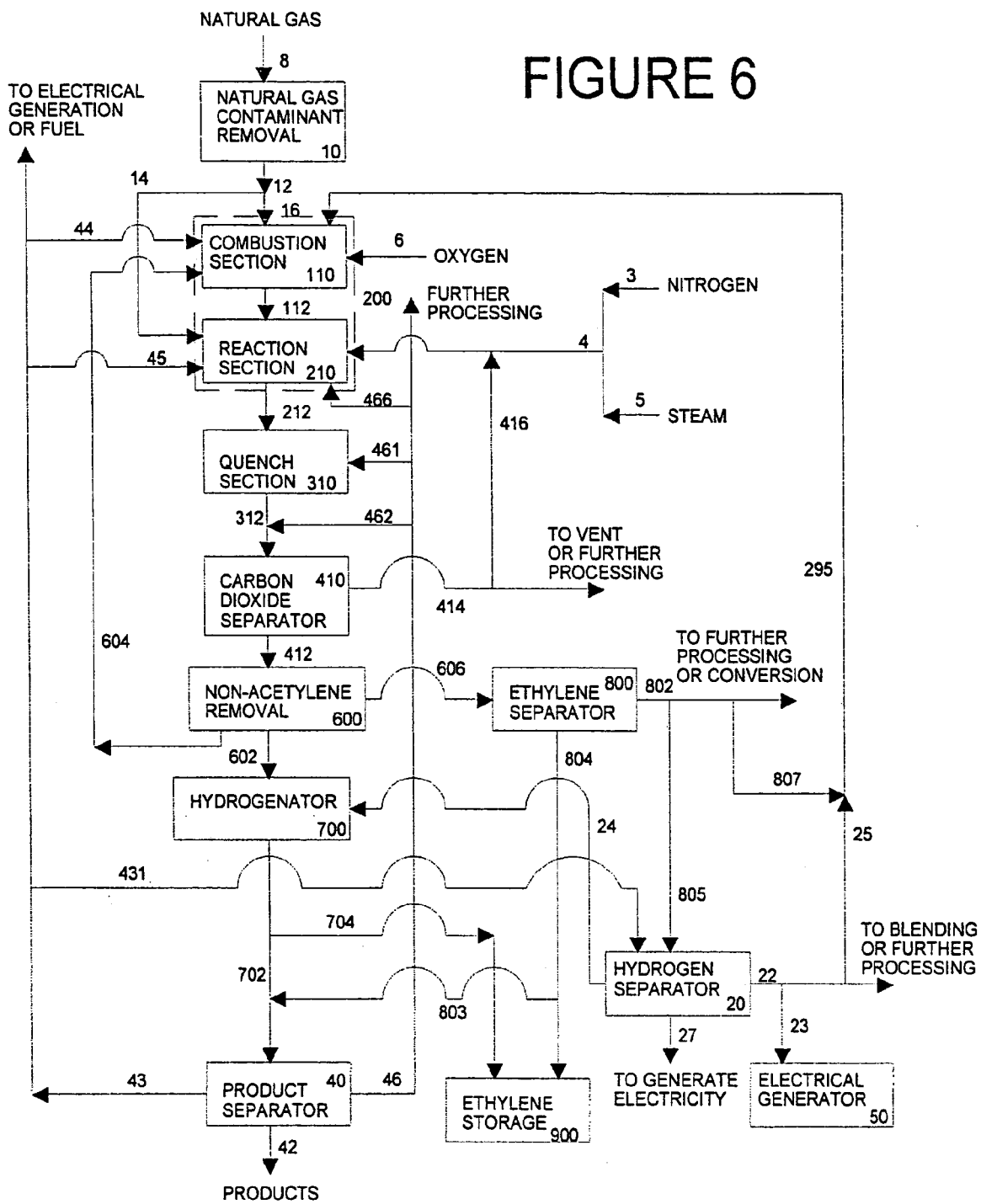
FIG. 6 is a schematic process flow diagram illustrating preferred embodiments of the process of the present invention in which the natural gas is heated to reaction temperature by burning a stream of natural gas and a portion of the stream comprising hydrogen (and, in some preferred embodiments, carbon monoxide produced with the reactive hydrocarbon products) in a mixed-stream reactor. The reaction products containing acetylene are subjected to separation, such that the acetylene is separated from the other gas components, and the acetylene stream is then hydrogenated. The other (non-acetylene) gas components may be vented, reserved for subsequent processing or chemical conversion, or returned to the process to be burned, further reacted or, after further separation, certain components of the reaction products gas stream may be combined with the acetylene hydrogenation product stream.

In other preferred embodiments, shown in FIG. 6, the reactor outlet stream produced by pyrolysis, containing reactive hydrocarbon components which comprise acetylene and ethylene as well as hydrogen, unreacted hydrocarbons, carbon monoxide, carbon dioxide and depending on the operation conditions, nitrogen, may be subjected to selective separation such that principally acetylene, the preferred reactive hydrocarbon product, is separated from the remaining products at non-acetylene removal 600. The stream 602 that contains acetylene may be selectively subjected to hydrogenation at hydrogenator 700 apart from the stream 412 from which it was removed. The stream 606 that has been reduced in acetylene concentration may be subject to gas separation techniques whereby the ethylene fraction, if in sufficient concentration, may be separated at ethylene separator 800 from the stream 802 of remaining components. If formed, this stream 804 of separated ethylene may be sent, in whole or in part, via stream 803 to product separator 40. Stream 803 may also be combined with a portion of stream 702 sent to product separator 40. Either ethylene stream 704 or 804, or both (separately or combined), can be reserved at ethylene storage 900 for recycle, conversion, purification, or export. Remaining components in stream 802, including but not limited to hydrogen, carbon dioxide, and carbon monoxide, and potentially unreacted hydrocarbons, nitrogen, and unseparated ethylene, as examples of components of this stream, can be recycled as feed, fuel, or both to reactor 200 via stream 807 and recycle stream 295, either entering the reactor directly or mixing with one or more of the other inlet streams. Stream 802 can also be sent to further processing (not shown). Depending on composition, stream 802 may comprise syngas, and could be, for example, used for methanol production or in Fisher-Tropsch reactions or units. Stream 802 can also be subjected to further separation, in some cases yielding a hydrogen stream. Stream 802, or streams separated from stream 802, can also be burned as fuel, used to generate electricity, flared, or vented.

Figure 7:
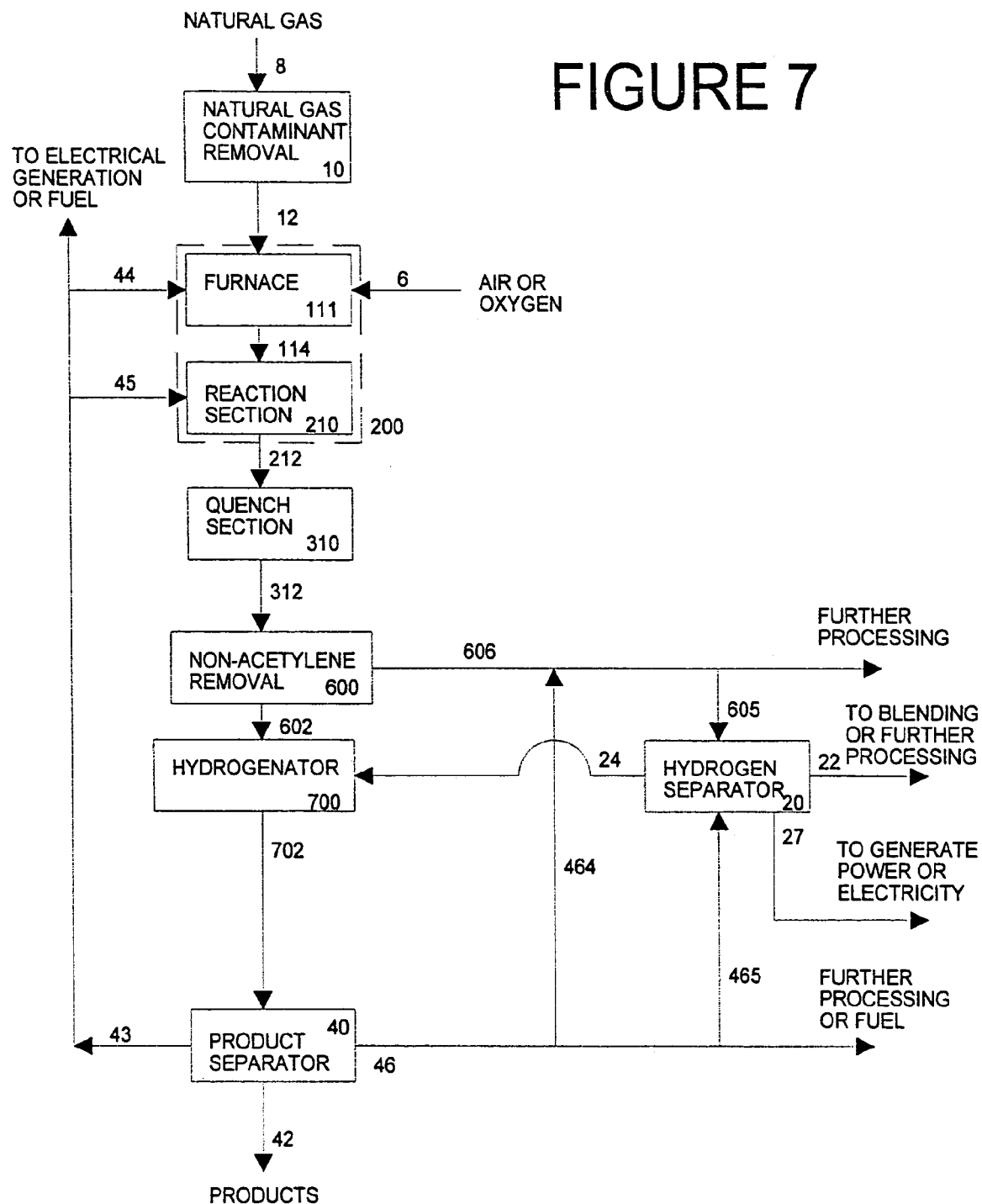
FIG. 7 is a schematic process flow diagram illustrating preferred embodiments of the process of the present invention in which the natural gas is heated to reaction temperature by burning a portion of the natural gas in a furnace. Acetylene is separated from the reaction products and hydrogenated. The other (non-acetylene) gas components may be vented, reserved for subsequent processing or chemical conversion, or returned to the process to be burned or further reacted.

In other preferred embodiments, shown in FIG. 7, the natural gas stream 12 is directed through furnace 111, which is heated in part by combustion with oxidant provided by oxidant stream 6, preferably comprising air or oxygen, such that sufficient temperature is created for a sufficient yet controlled time to convert a portion of the natural gas stream to reactive hydrocarbon products, preferably comprising ethylene and acetylene, and most preferably acetylene, in reactor 200. The reaction duration is limited, as described above, by quench section 310 wherein a fluid, such as water, heavy hydrocarbon, inorganic liquid, steam or other fluid is added in sufficient quantity to abate further reaction. As previously stated, quenching can be accomplished in multiple steps using different means, fluids, or both, or can be done in a single step using a single means or fluid. The gas stream 312 that emerges from the quench section 310 may be subjected to non-acetylene removal 600 such that the acetylene containing stream 602 is passed on to hydrogenator 700. The hydrogenator 700 outlet stream 702 may be subjected to separation in product separator 40 in which the desired products are removed. Gas removed from separator 40 as stream 43 may be recycled via stream 45 to the reaction section 210 of reactor 200 as supplemental feed, sent via stream 44 to furnace 111 of reactor 200 as fuel for combustion, or both. A portion of the gas removed from separator 40 as stream 46 may be combined via stream 464 in whole or in part with stream 606 from non-acetylene removal 600 and sent to further processing. Depending on composition, stream 606, or the combination of streams 606 and 464, may comprise syngas. A portion of stream 46 may be routed to hydrogen separator 20 either directly via stream 465 or indirectly via streams 464, 606 and 605, particularly, for example, in cases in which stream 46 contains substantial but impure hydrogen. A portion of stream 46 can also be burned as fuel, used to generate electricity, sent to further processing, flared, or vented.

Figure 8:
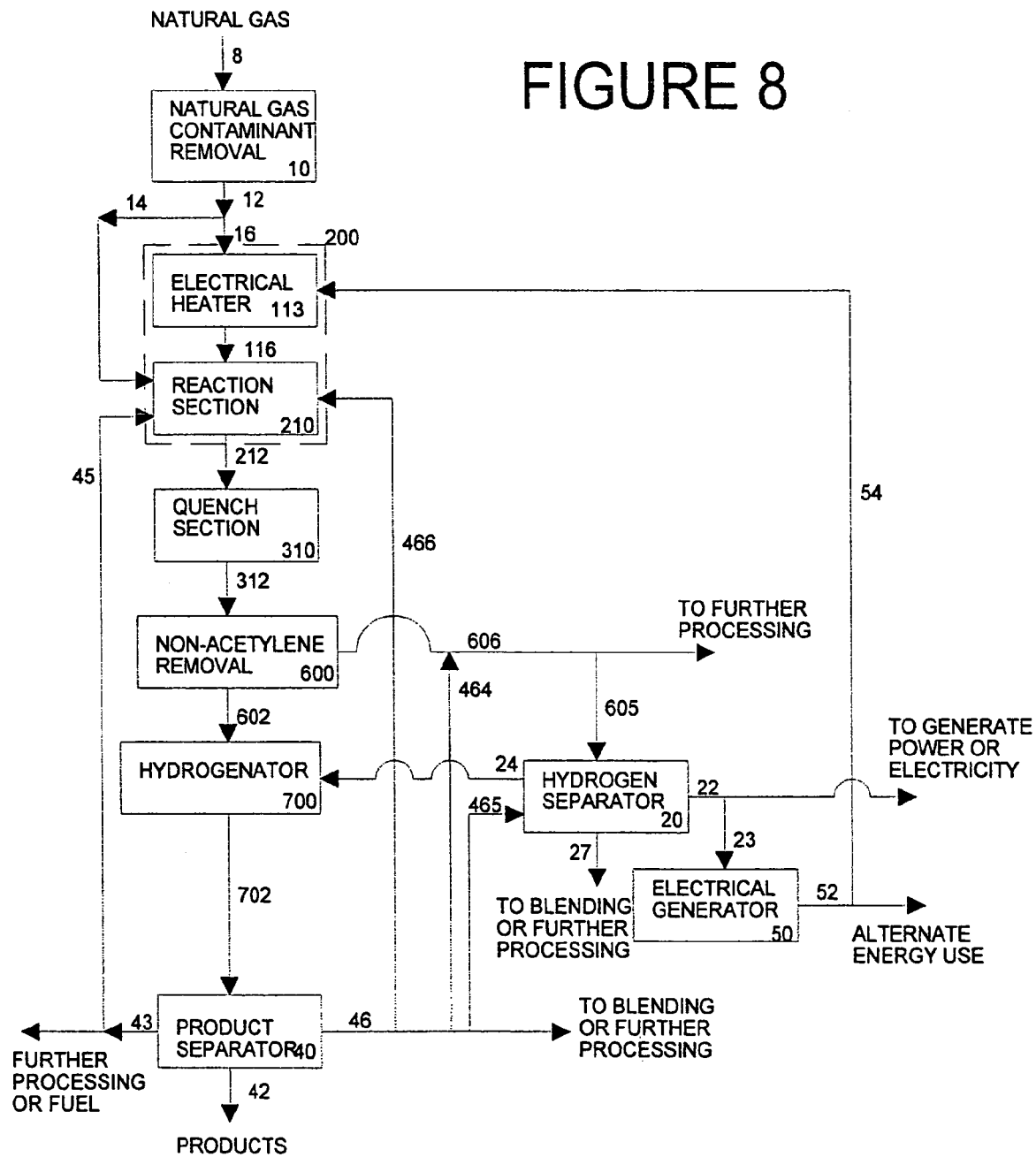
FIG. 8 is a schematic process flow diagram illustrating preferred embodiments of the process of the present invention in which the natural gas is heated to reaction temperature by an electrical heating device.

In other preferred embodiments, shown in FIG. 8, the natural gas stream 16 is directed through an electrical heater 113 and is heated by electrical energy such that adequate temperature is created for a sufficient yet controlled time to convert a portion of the natural gas stream to reactive hydrocarbon products, preferably comprising ethylene and acetylene, and most preferably acetylene, in reactor 200. Depending on the configuration of reactor 200 used, outlet stream 116 from electrical heater 113 to reaction section 210 may not be isolatable. A portion of the gas removed from separator 40 as stream 46 may be recycled to reactor 200 through stream 466, particularly if the gas contains substantial quantities of hydrocarbons. The acetylene-lean stream 606 via stream 605 may be subjected to further separation at separator 20 such that a hydrogen stream 22 is created, a portion of which as stream 23 can be used to generate electricity in electrical generator 50 as described previously. A notable but not exclusive use for the electrical power produced in generator 50, schematically shown as energy stream 52, is to provide the energy required by heater 113 such as depicated with energy stream 54. Various streams created in the process, such as, for example, streams 22, 27, 43, 46, and 606, may be used to generate electricity in external facilities not shown. Power produced either in generator 50 or in external facilities may be used to satisfy a portion of the electrical needs of the process.

Figure 9:
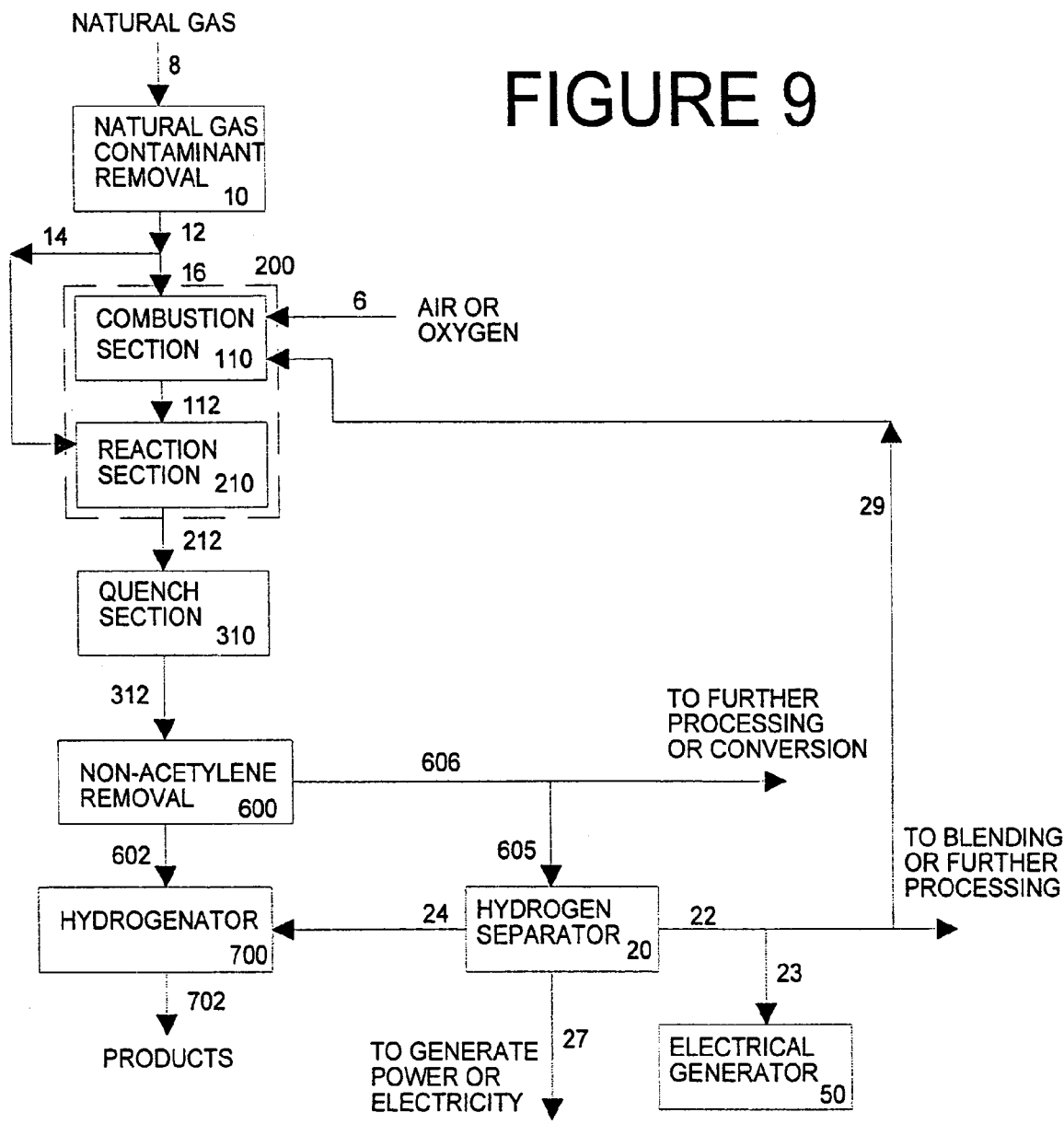
FIG. 9 is a schematic process flow diagram illustrating preferred embodiments of the process of the present invention in which the natural gas is heated to reaction temperature by means that may include hydrogen combustion in a combustion device.

In other preferred embodiments, shown in FIG. 9, the process is enhanced by utilization of a portion of the recovered hydrogen via stream 29 as fuel to be used in combustion section 110.

Figure 10:
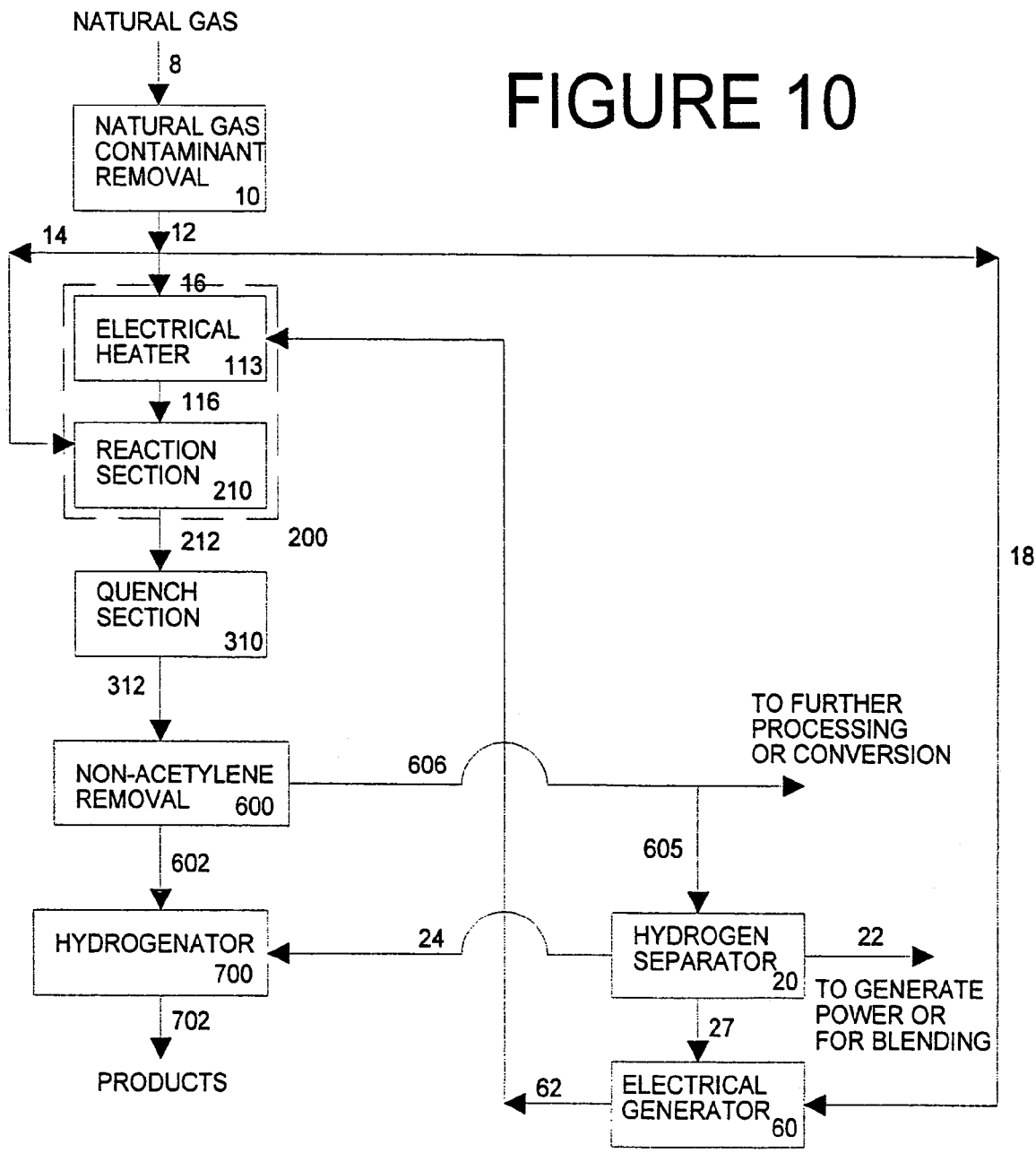
FIG. 10 is a schematic process flow diagram illustrating preferred embodiments of the process of the present invention in which the natural gas is heated to reaction temperature by an electrical heater via the electrical energy produced from hydrogen and a portion of the natural gas.

In other preferred embodiments, shown in FIG. 10, the process as described in FIG. 8 is practiced such that natural gas via stream 18 may be utilized as fuel for the electrical generator 60 that provides power via energy stream 62 to the electrical heater 113. Other streams created in the process that are suitable for generation of electricity may be sent in whole or in part to generator 60 as supplemental fuel to reduce the flow of stream 18. Hydrogen produced in the various steps of the process, such as cracking, may be separated out and utilized for purposes other than electrical power generation exclusively, for example, as further illustrated in the drawing figures.

Figure 11:
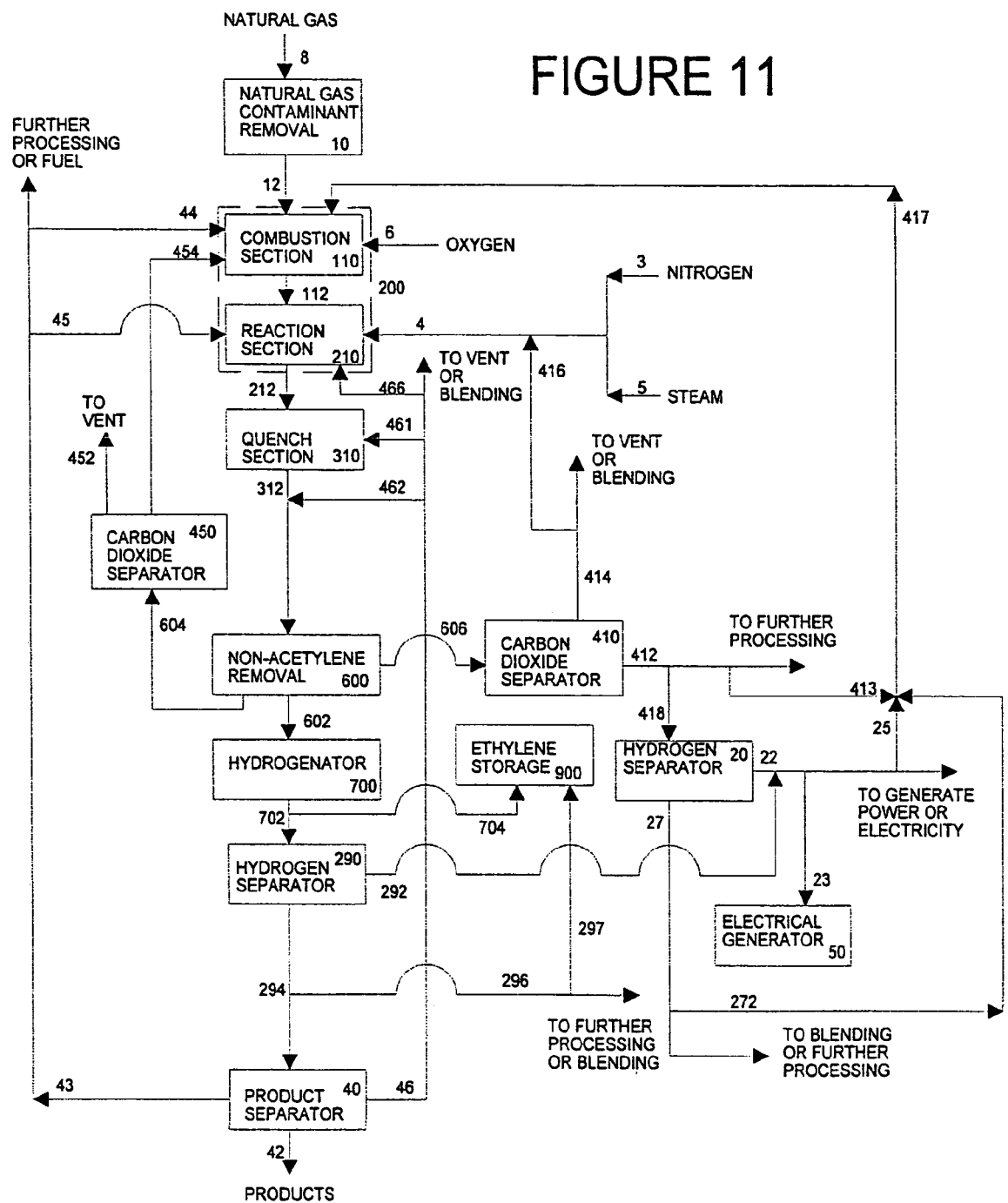
FIG. 11 is a schematic process flow diagram illustrating preferred embodiments of the process of the present invention in which the natural gas is heated to reaction temperature by incomplete combustion in a mixed stream reactor. Acetylene is separated from the reactive hydrocarbon products and non-hydrocarbons remaining in the quenched stream and then hydrogenated. Excess hydrogen may be removed in a hydrogen separation step downstream of the hydrogenator. Carbon dioxide may be removed from the process. The hydrogen-rich stream from the hydrogen separation step may be conveyed to an electrical generator or combined with hydrogen from the acetylene separation, or they may be utilized separately, as fuel in the electrical generator, as fuel in the process, or in subsequent chemical conversion steps. This process description applies equally to complete combustion, pyrolysis, and partial oxidation, as well as other direct and indirect heating methods that may be used to reach reaction temperature, except that stream compositions may be expected to vary accordingly.

In other preferred embodiments, shown in FIG. 11, natural gas is heated to reaction temperature by incomplete combustion in reactor 200. The reactor outlet stream is quenched in quench section 310 to substantially stop chemical reaction(s). Acetylene may be separated at non-acetylene removal 600 from the other reactive hydrocarbon products and non-hydrocarbons, and the acetylene-rich stream 602 may be subjected to hydrogenation at hydrogenator 700. The product of hydrogenation, principally ethylene, may be subjected thereafter to separation at product separator 40 or sent via stream 704 to ethylene storage 900 for later processing. Hydrogen, if there is excess, may be removed at separator 290 from the outlet stream 702 of the hydrogenator 700 via stream 292. The remaining components of the separator 290 outlet stream 294 may be conveyed to product separator 40. A portion of stream 294 may be removed from the process via stream 296 as a product comprising ethylene. A portion of stream 296 may be sent via stream 297 to ethylene storage 900. A portion of the acetylene lean gas from non-acetylene removal 600 represented as stream 604 may be sent through carbon dioxide separator 450, where some of the carbon dioxide present may be removed as stream 452, prior to sending the gas as stream 454 to be burned in combustion section 110 of reactor 200. Carbon dioxide may be removed from acetylene lean stream 606 via carbon dioxide separator 410 to stream 414, by which it may be removed from the process, or a portion of stream 414 may be recycled to reaction section 210 of reactor 200 via stream 416 and inlet stream 4 to reduce carbon formation or improve reaction yield. Sources of carbon dioxide other than stream 414 may be used, including, but not limited to, a portion of stream 452, another carbon dioxide recovery location within the process (not shown), or an external source. Outlet stream 412 from separator 410 may be returned in whole or in part via stream 413 and recycle stream 417 to reactor 200 to be burned as fuel, recycled as feed, or both. A portion of stream 412 may be burned as fuel, used to generate electricity, flared, or vented. Depending on composition, stream 606 or stream 412 may comprise syngas, or synthesis gas. A portion of either stream 606 or stream 412 may be sent to further processing (not shown). A portion of steam 412 may be sent via stream 418 to hydrogen separator 20. Stream 22 comprising hydrogen can be returned, in whole or in part, as streams 25 and 417 to reactor 200. A portion of hydrogen stream 22 may be sent to electrical generator 50 via stream 23. Hydrogen stream 292 from separator 290 may have the same disposition options as stream 22. Streams 292 and 22 can be combined as shown and used jointly, or they can be kept separate and used independently for the same purpose or different purposes. A portion of hydrogen lean gas outlet stream 27 from separator 20 can be recycled via streams 272 and 417 to be burned in combustion section 110 of reactor 200. Portions of stream 27 can also be used to generate electricity, burned as fuel, flared, or vented. This process description applies to complete combustion or pyrolysis as well as partial oxidation, with the exception that stream compositions may be expected to vary, as will be known to those skilled in the art.

Figure 12:
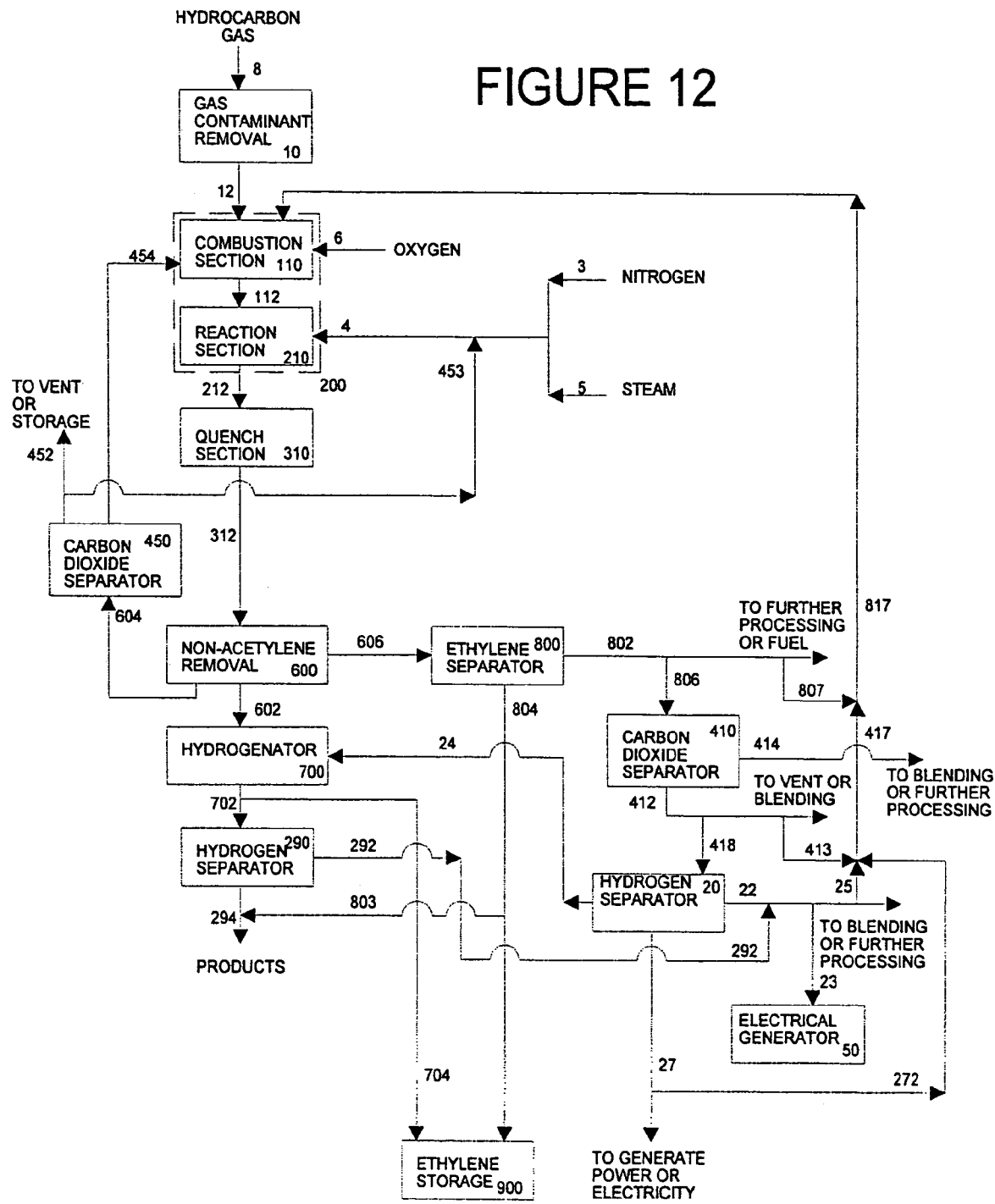
FIG. 12 is a schematic process flow diagram illustrating preferred embodiments of the process of the present invention that further comprise process steps in which ethylene is separated from the gas stream exiting the acetylene separation step that follows the quench section. The ethylene that is separated may be used in subsequent processing or chemical conversion.

In other preferred embodiments, such as those shown in FIG. 12, the process described above and illustrated in FIG. 11 may be modified such that the acetylene lean stream 606 formed from removal of acetylene at non-acetylene removal 600 downstream of the quench section 310 is subjected to separation techniques at ethylene separator 800 whereby the ethylene fraction, if in sufficient concentration and quantity, may be separated from the stream 802 of remaining components. If formed, this stream 804 of separated ethylene may be recombined in whole or in part via stream 803 with the hydrogen separator 290 outlet stream 294 to form a combined stream, comprising reactive gaseous products comprising ethylene, portions of which may be recycled, sent to storage, exported or sent to further processing, such as, for example, conversion, purification, or both. Streams 294 and 803 may also be sent separately from the process (not shown) as they may likely differ in composition, making different dispositions preferable. Either ethylene stream 704 or stream 804, or both (separately or combined), can be reserved at ethylene storage 900 for recycle, conversion, purification, or export. A portion of separator 800 outlet stream 802 may be recycled to reactor 200 via stream 807 and recycle stream 817. It may be desirable to remove some carbon dioxide from stream 802, which may be done by sending a portion of stream 802 via stream 806 through carbon dioxide separator 410, such as, for example, to limit accumulation of carbon dioxide in the process when recycling a portion of the outlet stream 412 to reactor 200 via stream 413 and recycle streams 417 and 817. Another example for desiring some carbon dioxide removal would be to benefit the hydrogen separator 20 by increasing performance or efficiency, or by reducing equipment size or costs, or some combination thereof. Since streams 802 and 412 may comprise syngas, still another example for desiring some carbon dioxide removal would be to alter the stoichiometric ratio of the syngas, as is well understood in the art, prior to sending to further processing (not shown). It will be easily recognized that carbon dioxide may be separated from other streams or locations within the process that are not designated in FIG. 12 as removal sites. It will also be easily recognized by those skilled in the art that separator 410 could be located upstream of separator 800 and fed with a portion of stream 606, which is the reverse order from that shown. A portion of stream 452 comprising carbon dioxide may be added to reactor 200 via stream 453 and inlet stream 4.

Figure 13:
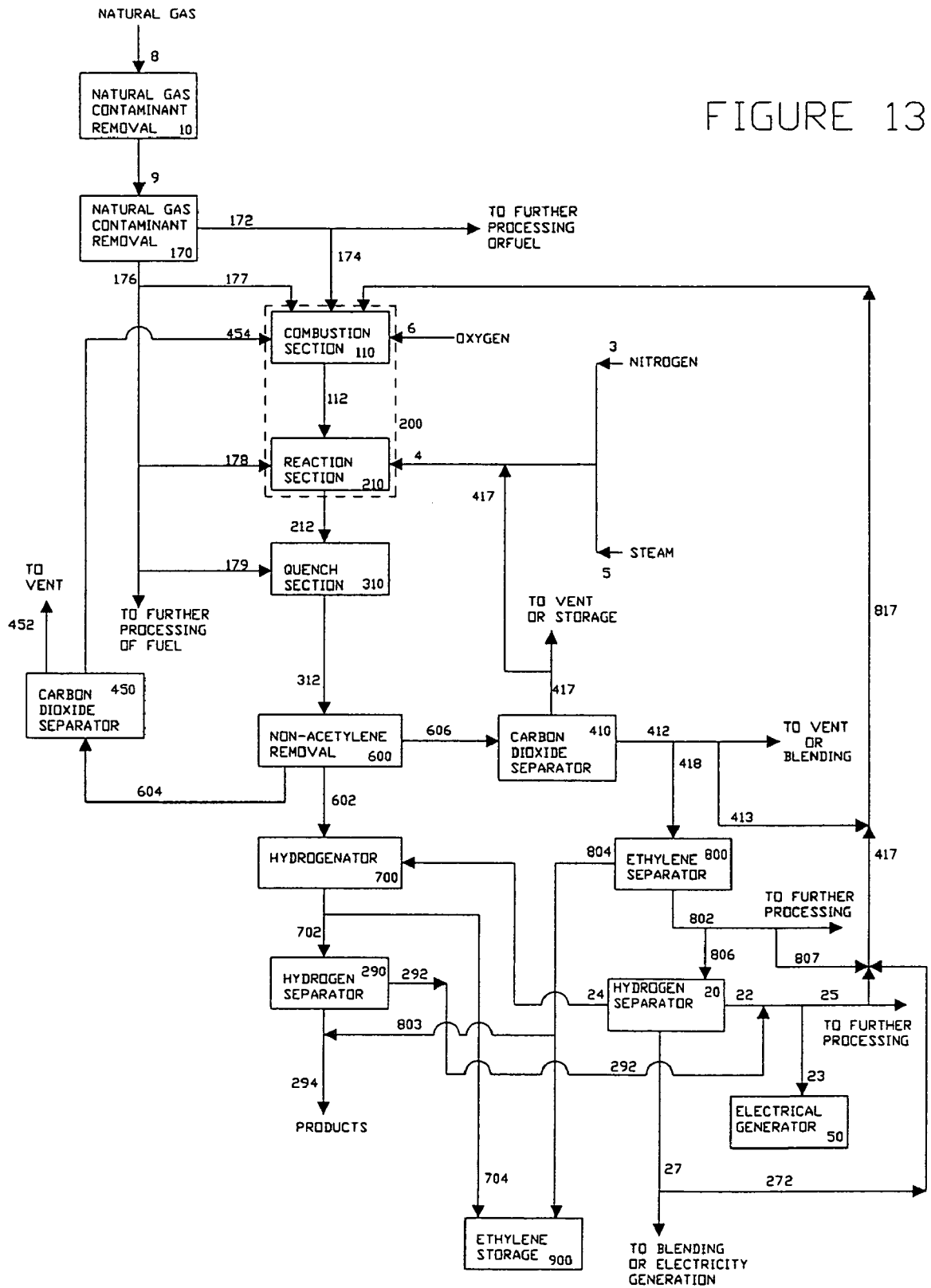
FIG. 13 is a schematic process flow diagram illustrating preferred embodiments of the process of the present invention in which the produced natural gas is split into at least two streams; one containing mostly methane, and at least one containing ethane and heavier components. These at least two streams can be reacted separately in two different reactors (or reacted in the same reactor but in different sections) that maintain different process conditions, depending on process needs. The separated natural gas fractions may be used to make the same product or different products.

In other preferred embodiments, shown in FIG. 13, the process described above and shown in FIG. 12 is modified such that the natural gas stream 9, which may have been subjected to contaminant removal at natural gas contaminant removal 10, is separated at natural gas separator 170 into at least two streams, one stream 172 that is rich in methane and one stream 176 that is lean in methane. The separation of natural gas into two or more streams of different composition allows additional flexibility in selection of the manner in which each stream will be utilized in subsequent processing, such as, by way of illustration and not limitation, combustion, cracking, or quenching. A portion of methane rich stream 172 may be sent to reactor 200 via stream 174. A portion of the methane lean stream 176, comprising ethane and heavier hydrocarbons, may be sent to combustion section 110 through stream 177, to reactor section 210 through stream 178, to quench section 310 through stream 179, or to any combination of these. The separation of natural gas into two or more streams also allows for alternate, parallel, or separate processing of the different streams (not shown) as well as set aside for storage. Processing paths may be recombined at any location within the process judged to be efficient or economical or beneficial.

In other preferred embodiments, electricity generator 50 may comprise a fuel cell or cells. With respect to fuel cells, any fuel cell design that uses a hydrogen stream and an oxygen steam may preferably be used, for example by way of illustration and not limitation, polymer electrolyte, alkaline, phosphoric acid, molten carbonate, and solid oxide fuel cells. The heat generated by the fuel cell or a turbine or turbines, may be used to boil the water exiting the fuel cell, thus forming steam. This resulting steam may then preferably be used to generate electricity, for instance in a steam turbine (not shown but within the scope of electrical generator 50, as is well known in the art). The electricity may then be sold or, as shown in for example FIG. 8, may be used to provide heat to preheat any of the appropriate feed, fuel, or oxidant streams, or to provide heat to other process equipment, such as, but not limited to, pumps, compressors, fans, and other conventional equipment that may be employed to accomplish the goals of the embodiments of the above-described processes of the present invention. In other preferred embodiments, such as those shown in FIG. 3, hydrogen as indicated at stream 22 from hydrogen separator 20 may preferably be produced as a saleable product. In still other preferred embodiments, such as those illustrated in FIG. 11, recycle stream 417 may preferably be burned directly in combustion section 110. In other preferred embodiments, such as those illustrated in FIG. 10, a portion of inlet gas stream 12 may be separated and routed via supplemental gas stream 18 to electrical generator 60. In this way, additional electrical power may be generated as described above. As will be understood by those skilled in the art, the electrical generators 50 or 60, or both in the above-described preferred embodiments may be eliminated from the process entirely so as to maximize hydrogen production for other purposes, such as, for example, direct combustion, storage, or alternate chemical conversion.

In still other preferred embodiments, as shown for example in FIGS. 11 and 12, the acetylene containing stream may be directed to hydrogenation reactor 700, where alkynes, preferably acetylene, may be converted into a preferred intermediate product, preferably comprising ethylene and other olefins. The non-acetylene containing stream(s) that flow(s) from the non-acetylene removal 600 may be redirected to the combustion section 110 of the reactor 200 via stream 604, and/or further separated into its components via stream 606, which preferably substantially comprises hydrogen, but which may comprise some carbon monoxide and smaller amounts of nitrogen, methane, ethylene, ethane, and other light gases, as is known in the art. The hydrogen, carbon monoxide, or mixture can be reserved for subsequent chemical reaction or conversion, or returned to the combustion section 110 of reactor 200, or used to produce electrical power through combustion or other means as have been described above, or conventional methods that are known to those skilled in the art. If sufficient ethylene is present in the stream from which acetylene is removed, as shown in the case of stream 606 in the preferred embodiments illustrated in FIG. 12, this ethylene may be separated out at ethylene separator 800 as an individual product stream or combined, in whole or in part with the product of the hydrogenator 700, which preferably comprises substantially ethylene, thereby maximizing the amount of ethylene product.

Traditional catalysts for conversion of alkynes to alkenes may preferably be used to convert acetylene to ethylene. These include nickel-boride, metallic palladium, and bimetallic catalysts such as palladium with a Group IB metal (copper, silver or gold). Some natural gas feed streams may contain trace amounts of sulfur, selenium or mercury compounds that may act as a poison for the hydrogenation catalyst. Accordingly, incoming sulfur compounds may react to form catalyst poisons, such as COS and $H_2S$. It is preferable to remove or reduce the concentration of these catalyst poisons by processes well known to those in the art, such as activated carbon or amine based processes, and most preferably by zinc oxide processes.

In accordance with the above preferred embodiments, it should be noted that the products of the reactions within hydrogenator 700 may be conveyed to hydrogen separator 290 through hydrogenation outlet stream 702. Because the conversion from acetylene to ethylene may not always be complete, hydrogenation outlet stream 702 may contain both acetylene and ethylene, as well as hydrogen and some higher molecular weight alkynes and alkenes.

In other preferred embodiments, product stream 606 from non-acetylene removal 600 may be routed variously to a secondary hydrogen separator 20, illustrated for example in FIGS. 11–13. Like hydrogen separator 290, this hydrogen separator 20 may be operated according to any of a variety of processes, including membrane or pressure swing processes, described for example in A. Malek and S. Farooq, "Hydrogen Purification from Refinery Fuel Gas by Pressure Swing Adsorption", AIChE J. 44, 1985 (1998), which is hereby incorporated herein by reference for all purposes.

In an alternate preferred embodiment, the produced natural gas 8 provided may be sufficiently pure that contaminant removal is not required. In such a case, the contaminant removal 10 may preferably be by-passed or eliminated. The necessity of performing contaminant removal will depend upon the nature of the contaminants, the catalyst used, if any, in the hydrogenator 700, the materials of construction used throughout the process, and the operating conditions.

In other preferred embodiments, separation of reactive gaseous products downstream of hydrogenator 700 may not be required or desirable depending on the intended disposition of the stream. In such cases, the downstream equipment comprising the product separator 40, may preferably not be operated continuously or even at all; separator 40 may not even exist in certain installations of the process.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The examples provided in the disclosure are presented for illustration and explanation purposes only and are not intended to limit the claims or embodiment of this invention. While the preferred embodiments of the invention have been shown and described, modification thereof can be made by one skilled in the art without departing from the spirit and teachings of the invention. Process design criteria, pendant processing equipment, and the like for any given implementation of the invention will be readily ascertainable to one of skill in the art based upon the disclosure herein. The embodiments described herein are exemplary only, and are not intended to be limiting. Many variations and modifications of the invention disclosed herein are possible and are within the scope of the invention. Use of the term "optionally" with respect to any element of the invention is intended to mean that the subject element is required, or alternatively, is not required. Both alternatives are intended to be within the scope of the invention.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

We claim:

1. A method for converting natural gas to reactive products, comprising:
   converting at least a portion of the natural gas to reactive hydrocarbon products, by
      heating the natural gas in a conversion reactor, comprising a reaction section operated at conversion promoting conditions, such that the reactive hydrocarbon products, comprising acetylene and ethylene, are produced, and further wherein a product stream comprising the reactive hydrocarbon products, carbon dioxide, carbon monoxide, and hydrogen is formed, quenching the product stream,
preparing an acetylene rich stream comprising carbon monoxide from the quenched product stream by intermediate processing, comprising separating at least one effluent stream comprising a non-acetylene component selected from the group consisting of carbon dioxide, hydrogen, carbon monoxide, light gases, syngas, ethylene, and combinations thereof, from the quenched product stream, and
conveying the acetylene rich stream to a hydrogenation reactor;
reacting acetylene and hydrogen in the hydrogenation reactor to form ethylene; and
conveying an ethylene rich stream from the hydrogenation reactor to storage of further processing.

2. The method of claim 1 wherein the conversion reactor is a non-catalytic reactor.

3. The method of claim 1 wherein the conversion reactor is a mixed-stream reactor.

4. The method of claim 1 wherein the intermediate processing further comprises:
separating a light gas rich stream from the quenched product stream, hydrogenating the acetylene rich stream.

5. The method of claim 1 wherein at least one effluent stream comprises hydrogen, and further comprising:
conveying the effluent stream comprising hydrogen to an electrical power generation device,
generating electrical power from the hydrogen and an oxygen containing stream,
heating the at least a portion of the natural gas that is converted to the reactive hydrocarbon products with the generated electrical power.

6. The method of claim 1 further comprising recycling at least one effluent stream from the intermediate processing to the conversion reactor.

7. The method of claim 6 wherein the at least a portion of the natural gas that is converted to the reactive hydrocarbon products is heated by products of combustion of a second portion of natural gas with an oxidant.

8. The method of claim 6 further comprising:
separating the ethylene rich stream into a reactive product stream comprising ethylene and a gas stream;
recycling the gas stream to the conversion reactor;
recovering the reactive product stream.

9. The method of claim 1, wherein the intermediate processing comprises separating a carbon dioxide rich effluent stream from the quenched product stream.

10. The method of claim 9 wherein the intermediate processing further comprises separating a hydrogen rich effluent stream from the quenched product stream.

11. The method of claim 9 wherein the intermediate processing further comprises separating a syngas rich effluent stream from the quenched product stream.

12. The method of claim 9 wherein the intermediate processing further comprises:
separating a light gas rich stream from the quenched product stream,
hydrogenating the acetylene rich stream.

13. The method of claim 12 wherein the intermediate processing further comprises separating a hydrogen rich stream from the quenched product stream.

14. A method for converting natural gas to reactive products, comprising:
providing a natural gas stream;
providing a feed stream comprising all or part of the natural gas stream;
providing a burn stream comprising combustible material;
conveying the feed stream and the burn stream to a reactor, wherein the burn stream is combusted with an oxidant, and the feed stream is heated by intimate mixing with the combustion products, to a sufficient temperature and for a sufficient time that a product stream comprising reactive products, carbon dioxide, carbon monoxide, and hydrogen is formed;
quenching the product stream;
preparing an acetylene rich stream comprising carbon monoxide from the quenched product stream by intermediate processing, comprising separating at least one effluent stream comprising a non-acetylene component selected from the group consisting of carbon dioxide, hydrogen, carbon monoxide, light gases, syngas, ethylene, and combinations thereof, from the quenched product stream, and
conveying the acetylene rich stream to a hydrogenation reactor;
reacting acetylene and hydrogen in the hydrogenation reactor to form ethylene; and
conveying an ethylene rich stream from the hydrogenation reactor to storage or further processing.

15. The method of claim 14, further comprising removing contaminants from the natural gas stream.

16. The method of claim 14, further comprising passing at least a portion of the product stream to a separator in which some carbon dioxide is removed.

17. The method of claim 14, further comprising passing at least a portion of the product stream to a separator in which some hydrogen is removed.

18. The method of claim 17, further comprising passing at least a portion of the hydrogen to the reactor such that the burn stream comprises the removed hydrogen.

19. The method of claim 14 wherein the burn stream comprises a portion of the natural gas stream.

20. The method of claim 14, further comprising introducing water, steam, or both to the reactor.

21. The method of claim 14 wherein the pressure of the natural gas stream is between about 1 bar and about 20 bar.

22. The method of claim 14 wherein the feed stream is preheated to a temperature in the range of from about 400° K to about 1800° K.

23. The method of claim 14 wherein the burn stream is preheated to a temperature in the range of from about 400° K to about 1800° K.

24. The method of claim 14 wherein the oxidant is preheated to a temperature in the range of from about 400° K to about 1800° K.

25. The method of claim 22 wherein the feed stream is maintained at a temperature of at least 400° K for between about 0.1 and about 100 milliseconds.

26. The method of claim 25 wherein the feed stream is maintained at a temperature of at least 400° K for between about 0.2 and about 10 milliseconds.

27. The method of claim 14 wherein the oxidant comprises oxygen.

28. The method of claim 27 wherein the oxygen is supplied from a source selected from the group consisting of oxygen, purified oxygen, air, and oxygen-enriched air.

29. The method of claim 17, further comprising:
conveying hydrogen to a fuel cell or turbine;
providing oxygen to the fuel cell or turbine;
reacting the hydrogen with the oxygen in the fuel cell or burning the hydrogen with the oxygen in the turbine to produce electricity.

30. The method of claim 29 wherein the fuel cell or turbine produce heat and water.

31. The method of claim 30, further comprising:
heating the water produced in the fuel cell or turbine to form steam, and
generating electricity from the steam.

32. The method of claim 14 wherein the product stream is quenched using a device selected from the group consisting of a Joule-Thompson expander, nozzle, turbo expander, water spray, hydrocarbon spray, oil spray, steam, boiler, heat exchanger, and combinations thereof.

33. The method of claim 14 wherein the product stream is quenched by mixing the product stream with vapor or liquid hydrocarbons.

34. The method of claim 14, further comprising:
reacting at least a portion of the reactive products with the hydrogen to form ethylene.

35. The method of claim 14, further comprising separating a combustible gas or vapor from the process and using the gas or vapor as fuel.

36. The method of claim 14, further comprising separating a gas or vapor from the process and using the gas or vapor to generate electricity.

37. The method of claim 14 further comprising separating a combustible liquid or slurry from the process and using the liquid or slurry as fuel.

38. The method of claim 14, further comprising:
segregating a portion of the natural gas stream to form an electrical generation stream;
conveying the electrical generation stream to a fuel cell or turbine;
providing oxygen to the fuel cell or turbine; reacting the electrical generation stream with the oxygen in the fuel cell or the turbine to generate electricity.

39. A method for converting natural gas to reactive products, comprising:
providing a natural gas stream;
conveying the natural gas stream to a reactor wherein the natural gas stream is partially burned such that a portion of the natural gas is heated to a temperature adequate to produce hydrogen, carbon dioxide, carbon monoxide, and reactive products, said reactive products comprising acetylene;
quenching the reactive products and hydrogen;
preparing an acetylene rich stream comprising carbon monoxide from the quenched product stream by intermediate processing, comprising separating at least one effluent stream comprising a non-acetylene component selected from the group consisting of carbon dioxide, hydrogen, carbon monoxide, light gases, syngas, ethylene, and combinations thereof, from the quenched product stream, and
conveying the acetylene rich stream to a hydrogenation reactor;
reacting acetylene and hydrogen in the hydrogenation reactor to form ethylene; and
conveying an ethylene rich stream from the hydrogenation reactor to storage or further processing.

40. The method of claim 39, further comprising removing contaminants from the natural gas stream.

41. The method of claim 39, further comprising passing at least a portion of the reactive products to a separator in which some carbon dioxide is removed.

42. The method of claim 39, further comprising passing at least a portion of the reactive products and hydrogen to a separator in which at least some of the hydrogen is removed.

43. The method of claim 39, further comprising passing at least a portion of the reactive products to a separator in which some carbon monoxide is removed.

44. The method of claim 39 wherein the natural gas stream is preheated by a device selected from the group consisting of electric arc, resistance heater, plasma generator, fuel cell, combustion heater, heat exchanger, and combinations thereof.

45. The method of claim 39 wherein the pressure of the natural gas stream is between about 1 bar and about 20 bar.

46. The method of claim 39 wherein the natural gas stream is preheated to a temperature in the range of from about 400° K to about 1800° K.

47. The method of claim 46 wherein a portion of the natural gas is maintained at a temperature of at least 400° K for between about 0.1 and about 100 milliseconds.

48. The method of claim 47 wherein a portion of the natural gas is maintained at a temperature of at least 400° K for between about 0.2 and about 10 milliseconds.

49. The method of claim 42, further comprising:
conveying a portion of the hydrogen to a fuel cell or turbine;
providing an oxygen stream to the fuel cell or turbine;
reacting the hydrogen with the oxygen in the fuel cell or turbine to produce electricity.

50. The method of claim 49 wherein the fuel cell or turbine produce heat.

51. The method of claim 50, further comprising:
heating the water produced in the fuel cell with the heat produced in the fuel cell to generate steam and;
generating electricity from the steam.

52. The method of claim 39 wherein the reactive products are quenched by a device selected from the group consisting of a Joule-Thompson expander, nozzle, turbo expander, water spray, hydrocarbon spray, oil spray, steam, boiler, heat exchanger, and combinations thereof.

53. The method of claim 39 wherein the reactive products are quenched by mixing the product stream with vapor or liquid hydrocarbons.

54. The method of claim 39, further comprising introducing steam, water, or both to the reactor.

55. The method of claim 54 further comprising heating the steam, water, or both prior to its introduction to the reactor by a device selected from the group consisting of electric arc, resistance heater, plasma generator, fuel cell, combustion heater, heat exchanger, and combinations thereof.

56. The method of claim 39, further comprising separating a syngas stream from the process.

57. The method of claim 56, further comprising conveying at least a portion of the syngas stream to subsequent processing or conversion.

58. The method of claim 56, further comprising separating at least some carbon dioxide from at least a portion of the syngas stream.

59. The method of claim 56, further comprising separating hydrogen from at least a portion of the syngas stream.

60. The method of claim 59, further comprising using the hydrogen to generate electricity directly or indirectly.

61. The method of claim 39, further comprising separating a gas or vapor from the process and using the gas or vapor as fuel.

62. The method of claim 39, further comprising separating a gas or vapor from the process and using the gas or vapor to generate electricity.

63. The method of claim 39, further comprising separating a liquid or slurry from the process and using the liquid or slurry as fuel.

64. A method for converting natural gas to reactive products comprising ethylene, comprising:
providing a natural gas stream;
providing a feed stream comprising all or part of the natural gas stream;
providing a burn stream comprising combustible material;
conveying the feed stream and burn stream to a reactor wherein the burn stream is burned in a combustion section with an oxidant to heat the feed stream by intimate mixing with the combustion products to a temperature and for a time such that a reactive product stream comprising hydrogen, carbon dioxide, carbon monoxide, and reactive products is formed, said reactive products comprising acetylene;
quenching the reactive product stream;
separating from the reactive product stream an acetylene rich stream and a light gas stream, said light gas stream comprising carbon dioxide, carbon monoxide and hydrogen;
conveying the acetylene rich stream to a hydrogenation reactor;
reacting acetylene and hydrogen in the hydrogenation reactor to form ethylene;
conveying an ethylene rich stream from the hydrogenation reactor to storage or further processing.

65. The method of claim 64 wherein one, some, or all of the natural gas, feed, burn, and oxidant streams is or are preheated using a device selected from the group consisting of electric arc, resistance heater, plasma generator, fuel cell, combustion heater, heat exchanger, and combinations thereof.

66. The method of claim 64 wherein the pressure of the natural gas stream is between about 1 bar and about 20 bar.

67. The method of claim 64 further comprising removing contaminants from the natural gas stream.

68. The method of claim 64 wherein the burn stream comprises a portion of the natural gas stream.

69. The method of claim 64 wherein the burn stream comprises hydrogen.

70. The method of claim 64 wherein the feed stream is preheated to a temperature in the range of from about 400° K to about 1800° K.

71. The method of claim 64 wherein the burn stream is preheated to a temperature in the range of from about 400° K to about 1800° K.

72. The method of claim 64 wherein the oxidant is preheated to a temperature in the range of from about 400° K to about 1800° K.

73. The method of claim 64 wherein the natural gas stream is preheated to a temperature in the range of from about 400° K to about 1800° K.

74. The method of claim 70 wherein the feed stream is maintained at a temperature of at least 400° K for between about 0.1 and about 100 milliseconds.

75. The method of claim 74 wherein the feed stream is maintained at a temperature of at least 400° K for between about 0.2 and about 10 milliseconds.

76. The method of claim 64, further comprising separating some carbon dioxide from the reactive product stream.

77. The method of claim 64, further comprising separating some hydrogen from the reactive product stream.

78. The method of claim 77, further comprising conveying at least a portion of the hydrogen back to the reactor such that the hydrogen comprises all or part of the burn stream.

79. The method of claim 77, further comprising conveying at least a portion of the hydrogen to the hydrogenation reactor.

80. The method of claim 64, further comprising providing hydrogen to the hydrogenation reactor.

81. The method of claim 64 wherein the oxidant comprises oxygen.

82. The method of claim 77, further comprising:
conveying at least a portion of the hydrogen to a fuel cell or turbine;
providing oxygen to the fuel cell or turbine;
reacting the hydrogen with the oxygen in the fuel cell or burning the hydrogen with the oxygen in the turbine to produce electricity.

83. The method of claim 82 wherein the fuel cell or turbine produces heat.

84. The method of claim 83, further comprising:
heating water produced in the fuel cell using the heat produced in the fuel cell to form steam and;
generating electricity from the steam.

85. The method of claim 64 wherein the reactive product stream is quenched using a device selected from the group consisting of a Joule-Thompson expander, nozzle, turbo expander, water spray, hydrocarbon spray, oil spray, steam, boiler, heat exchanger, and combinations thereof.

86. The method of claim 64 wherein the reactive product stream is quenched at least partially by mixing the reactive product stream with vapor or liquid hydrocarbons.

87. The method of claim 64, further comprising:
separating a gas or vapor from the ethylene rich stream and recirculating a portion of the gas or vapor to the reactor.

88. The method of claim 64, further comprising:
separating a stream containing hydrogen from the ethylene rich stream;
separating hydrogen from the stream containing hydrogen.

89. The method of claim 64, further comprising:
separating a gas or vapor from the ethylene rich stream and using at least a portion of the gas or vapor to at least partially quench the reactive product stream.

90. The method of claim 64, further comprising:
separating a liquid stream from the ethylene rich stream.

91. The method of claim 90, further comprising:
using at least a portion of the liquid stream to at least partially quench the reactive product stream.

92. The method of claim 64, further comprising separating at least some hydrogen from the ethylene rich stream.

93. The method of claim 92, further comprising passing at least a portion of the hydrogen back to the reactor such that the hydrogen comprises all or part of the burn stream.

94. The method of claim 64, further comprising introducing nitrogen to the reactor.

95. The method of claim 64, further comprising introducing steam, water, or both to the reactor.

96. The method of claim 64, further comprising introducing carbon dioxide to the reactor.

97. The method of claim 96 wherein the carbon dioxide comprises carbon dioxide produced in the process.

98. The method of claim 94, further comprising heating the nitrogen prior to its introduction to the reactor with a device selected from the group consisting of electric arc, resistance heater, plasma generator, fuel cell, combustion heater, heat exchanger, and combinations thereof.

99. The method of claim 95, further comprising heating the steam, water, or both prior to introduction to the reactor with a device selected from the group consisting of electric arc, resistance heater, plasma generator, fuel cell, combustion heater, heat exchanger, and combinations thereof.

100. The method of claim 64, further comprising separating hydrogen from at least a portion of the light gas stream.

101. The method of claim 100, further comprising using a portion of the hydrogen to generate electricity directly or indirectly.

102. The method of claim 100, further comprising conveying at least a portion of the hydrogen to the reactor.

103. The method of claim 100, further comprising conveying at least a portion of the hydrogen to the hydrogenation reactor.

104. The method of claim 100, further comprising conveying a portion of the light gas stream from which some hydrogen has been removed to the reactor.

105. The method of claim 100, further comprising separating at least some carbon dioxide from at least a portion of the light gas stream from which some hydrogen has been removed.

106. The method of claim 64, further comprising separating a gas or vapor from the process and using the gas or vapor as fuel.

107. The method of claim 64, further comprising separating a gas or vapor from the process and using the gas or vapor to generate electricity.

108. The method of claim 64, further comprising separating a liquid or slurry from the process and using the liquid or slurry as fuel.

109. The method of claim 64, further comprising recirculating a portion of the light gas stream to the reactor.

110. The method of claim 64, further comprising separating at least some carbon dioxide from at least a portion of the light gas stream.

111. The method of claim 110, further comprising conveying a portion of the light gas stream from which some carbon dioxide has been removed to the reactor.

112. The method of claim 64, further comprising separating at least some ethylene from at least a portion of the light gas stream.

113. The method of claim 112, further comprising conveying a portion of the light gas stream from which some ethylene has been removed to the reactor.

114. The method of claim 112, further comprising conveying a portion of the ethylene to storage or to further processing outside the process.

115. The method of claim 112, further comprising separating at least some carbon dioxide from at least a portion of the light gas stream from which some ethylene has been removed.

116. The method of claim 64, further comprising separating hydrogen from the process and using a portion or portions of the hydrogen for one or more purposes selected from the group comprising:
  recirculating back to the reactor;
  conveying to the hydrogenation reactor;
  generating electricity directly or indirectly;
  burning as fuel;
  exporting for external use.

117. The method of claim 64, further comprising separating hydrogen from one or more sources within the process selected from the group comprising:
  a portion of the reactive product stream;
  a portion of the light gas stream;
  a portion of the light gas stream after some ethylene has been removed;
  a portion of the light gas stream after some carbon dioxide has been removed;
  a portion of the light gas stream after some ethylene and carbon dioxide have been removed;
  a portion of the hydrogenation reactor effluent.

118. A method for converting natural gas to reactive products comprising ethylene, comprising:
  providing a natural gas stream;
  conveying the natural gas stream to a reactor wherein the natural gas stream is partially burned with an oxidant such that a portion of the natural gas stream is heated to a temperature sufficient to convert some of the natural gas to form a reactive product stream comprising hydrogen, carbon dioxide, carbon monoxide, and reactive products comprising acetylene;
  quenching the reactive product stream;
  separating from the reactive product stream an acetylene rich stream and a light gas stream, said light gas stream comprising carbon dioxide, carbon monoxide, and hydrogen;
  conveying the acetylene rich stream to a hydrogenation reactor;
  reacting at least a portion of the acetylene rich stream with hydrogen in the hydrogenation reactor to form ethylene;
  conveying an ethylene rich stream from the hydrogenation reactor to storage or further processing.

119. The method of claim 118 further comprising removing contaminants from the natural gas stream.

120. The method of claim 118 wherein the pressure of the natural gas stream is between about 1 bar and about 20 bar.

121. The method of claim 118, further comprising preheating the natural gas stream to a temperature in the range of from about 400° K to about 1800° K.

122. The method of claim 121, further comprising maintaining a portion of the natural gas stream at a temperature of at least 400° K for between about 0.1 and about 100 milliseconds.

123. The method of claim 122, further comprising maintaining a portion of the natural gas stream at a temperature of at least 400° K for between about 0.2 and about 10 milliseconds.

124. The method of claim 118, further comprising preheating the oxidant to a temperature in the range of from about 400° K to about 1800° K.

125. The method of claim 118, further comprising separating at least some carbon dioxide from the reactive product stream.

126. The method of claim 118, further comprising separating at least some hydrogen from the reactive product stream.

127. The method of claim 118, further comprising separating at least some carbon monoxide from the reactive product stream.

128. The method of claim 118, further comprising introducing nitrogen to the reactor.

129. The method of claim 128, further comprising heating the nitrogen prior to its introduction to the reactor by a device selected from the group consisting of electric arc, resistance heater, plasma generator, fuel cell, combustion heater, heat exchanger, and combinations thereof.

130. The method of claim 118, further comprising introducing steam, water, or both to the reactor.

131. The method of claim 130, further comprising heating the steam, water, or both prior to introduction to the reactor by a device selected from the group consisting of electric arc, resistance heater, plasma generator, fuel cell, combustion heater, heat exchanger, and combinations thereof.

132. The method of claim 118, further comprising introducing carbon dioxide to the reactor.

133. The method of claim 132 wherein a portion of the carbon dioxide has been separated from the process and recirculated to the reactor.

134. The method of claim 118, further comprising conveying hydrogen to the reactor.

135. The method of claim 118, further comprising providing hydrogen to the hydrogenation reactor.

136. The method of claim 118 wherein the oxidant comprises oxygen.

137. The method of claim 118 wherein the natural gas stream, the oxidant, or both, are preheated by a device selected from the group consisting of electric arc, resistance heater, plasma generator, fuel cell, combustion heater, heat exchanger, and combinations thereof.

138. The method of claim 118, further comprising:
separating a portion of the hydrogen from a portion of the light gas stream;
conveying a portion of the hydrogen to a fuel cell or turbine;
providing oxygen to the fuel cell or turbine;
reacting the hydrogen with the oxygen in the fuel cell or burning the hydrogen with the oxygen in the turbine to produce electricity.

139. The method of claim 138 wherein the fuel cell or turbine further produce water and heat.

140. The method of claim 138, further comprising:
heating the water produced in the fuel cell with the heat produced in the fuel cell to form steam;
generating electricity from the steam.

141. The method of claim 118 wherein the reactive product stream is quenched by a device selected from the group consisting of a Joule-Thompson expander, nozzle, turbo expander, water spray, hydrocarbon spray, oil spray, steam, boiler, heat exchanger, and combinations thereof.

142. The method of claim 118 wherein the reactive product stream is quenched at least partially by mixing the reactive product stream with vapor or liquid hydrocarbons.

143. The method of claim 118 wherein the reactive product stream is quenched at least partially by mixing the reactive product stream with relatively cooler fluids.

144. The method of claim 118, further comprising recirculating a portion of the light gas stream to the reactor.

145. The method of claim 118, further comprising separating at least some carbon dioxide from at least a portion of the light gas stream.

146. The method of claim 145, further comprising conveying a portion of the light gas stream from which some carbon dioxide has been removed to the reactor.

147. The method of claim 118, further comprising separating at least some ethylene from at least a portion of the light gas stream.

148. The method of claim 147, further comprising conveying a portion of the ethylene to storage or to further processing outside the process.

149. The method of claim 147, further comprising separating at least some carbon dioxide from at least a portion of the light gas stream from which some ethylene has been removed.

150. The method of claim 118, further comprising separating at least some hydrogen from the hydrogenation reactor effluent.

151. The method of claim 118, further comprising separating a syngas stream from the process.

152. The method of claim 118 wherein the light gas stream comprises syngas.

153. The method of claim 151, further comprising conveying at least a portion of the syngas stream to subsequent processing or conversion.

154. The method of claim 151, further comprising separating at least some carbon dioxide from a least a portion of the syngas stream.

155. The method of claim 154, further comprising conveying a portion of the syngas stream from which some carbon dioxide has been removed to the reactor.

156. The method of claim 151, further comprising separating hydrogen from a least a portion of the syngas stream.

157. The method of claim 156, further comprising separating at least some carbon dioxide from at least a portion of the syngas stream from which some hydrogen has been removed.

158. The method of claim 156, further comprising using a portion of the hydrogen to generate electricity directly or indirectly.

159. The method of claim 156, further comprising conveying a portion of the hydrogen to the hydrogenation reactor.

160. The method of claim 151, further comprising conveying at least a portion of the syngas stream to the reactor.

161. The method of claim 151, further comprising separating at least some ethylene from at least a portion of the syngas stream.

162. The method of claim 118, further comprising separating hydrogen from the process and using a portion or portions of the hydrogen for one or more purposes selected from the group comprising:
recirculating back to the reactor;
conveying to the hydrogenation reactor;
generating electricity directly or indirectly;
burning as fuel;
blending with other process streams;
exporting for external use.

163. The method of claim 118, further comprising separating hydrogen from one or more sources within the process selected from the group comprising:
a portion of the reactive product stream;
a portion of the light gas stream;
a portion of a syngas stream;
a portion of the light gas stream after some ethylene has been removed;
a portion of the syngas stream after some ethylene has been removed;
a portion of the light gas stream after some carbon dioxide has been removed;
a portion of the syngas stream after some carbon dioxide has been removed;
a portion of the light gas stream after some ethylene and carbon dioxide have been removed;
a portion of the syngas stream after some ethylene and carbon dioxide have been removed;
a portion of the hydrogenation reactor effluent.

164. The method of claim 118, further comprising:
separating a gas or vapor from the ethylene rich stream and recirculating a portion of the gas or vapor to the reactor.

165. The method of claim 118, further comprising:
separating a stream containing hydrogen from the ethylene rich stream;
separating hydrogen from the stream containing hydrogen.

166. The method of claim 118, further comprising:
separating a gas or vapor from the ethylene rich stream and using at least a portion of the gas or vapor to at least partially quench the reactive product stream.

167. The method of claim 118, further comprising:
separating a liquid from the ethylene rich stream.

168. The method of claim 167, further comprising:
using at least a portion of the liquid to at least partially quench the reactive product stream.

169. The method of claim 118, further comprising separating a gas or vapor from the process and using the gas or vapor as fuel.

170. The method of claim 118, further comprising separating a gas or vapor from the process and using the gas or vapor to generate electricity.

171. The method of claim 118, further comprising separating a liquid or slurry from the process and using the liquid or slurry as fuel.

172. A method for converting natural gas to ethylene and reactive products, comprising:
providing a natural gas stream;
providing a feed stream comprising all or part of the natural gas stream;
conveying a burn stream comprising combustible material to a furnace wherein the burn stream is burned with an oxidant comprising oxygen;
conveying the feed stream to a reactor wherein the feed stream is heated by indirect heat transfer with the combustion products of the burn stream and oxidant to a temperature and for a time sufficient to form a reactive product stream comprising acetylene, carbon dioxide, carbon monoxide and hydrogen;
quenching the reactive product stream;
separating from the reactive product stream an acetylene rich stream, and a light gas stream, said light gas stream comprising carbon dioxide, carbon monoxide and hydrogen;
conveying the acetylene rich stream to a hydrogenation reactor;
reacting acetylene and hydrogen in the hydrogenation reactor to form ethylene;
conveying an ethylene rich stream from the hydrogenation reactor to storage or further processing.

173. The method of claim 172, wherein the burn stream comprises a portion of the natural gas stream, a portion of a stream separated from the process, or both.

174. The method of claim 172, further comprising removing contaminants from the natural gas stream.

175. The method of claim 172, further comprising:
providing a second feed stream comprising a portion of the natural gas stream, a portion of a stream separated from the process, or both;
conveying the second feed stream to a reaction section of the reactor wherein the second feed stream is heated by intimate mixing with the feed stream to a temperature and for a time sufficient such that reactive products comprising acetylene, ethylene, or both, are produced;
wherein the feed stream is heated and not reacted, partially reacted, or completely reacted prior to mixing with the second feed stream; and
wherein the reactive products produced from the second feed stream are mixed with the reactive products produced from the feed stream to form an improved reactive product stream.

176. The method of claim 172 wherein the pressure of the natural gas stream is between about 1 bar and about 20 bar.

177. The method of claim 172 wherein the natural gas stream is preheated to a temperature in the range of from about 400° K to about 1800° K.

178. The method of claim 172 wherein the feed stream is preheated to a temperature in the range of from about 400° K to about 1800° K.

179. The method of claim 178 wherein the feed stream is maintained at a temperature of at least 400° K for between about 0.1 and about 100 milliseconds.

180. The method of claim 179 wherein the feed stream is maintained at a temperature of at least 400° K for between about 0.2 and about 10 milliseconds.

181. The method of claim 172, further comprising conveying a portion of the light gas stream to the furnace as fuel.

182. The method of claim 172, further comprising:
separating hydrogen and other gases from at least a portion of the light gas stream.

183. The method of claim 182, further comprising:
conveying a portion of the hydrogen to a fuel cell or turbine;
providing oxygen to the fuel cell or turbine;
reacting the hydrogen with the oxygen in the fuel cell or burning the hydrogen with the oxygen in the turbine to produce electricity.

184. The method of claim 183 wherein the fuel cell or turbine also produce heat and water.

185. The method of claim 184, further comprising:
heating the water produced in the fuel cell with the heat produced in the fuel cell to form steam and;
generating electricity from the steam.

186. The method of claim 172 wherein the reactive product stream is quenched by a device selected from the group consisting of a Joule-Thompson expander, nozzle, turbo expander, water spray, hydrocarbon spray, oil spray, steam, boiler, heat exchanger, and combinations thereof.

187. The method of claim 172 wherein the reactive product stream is quenched at least partially by mixing the reactive product stream with vapor or liquid hydrocarbons.

188. The method of claim 172 wherein the natural gas stream, the feed stream, or both, is or are preheated by a device selected from the group consisting of electric arc, resistance heater, plasma generator, fuel cell, heat exchanger, and combinations thereof, or wherein the natural gas stream, the feed stream, or both, is or are heated by combustion of a portion of the natural gas stream or other combustible stream.

189. The method of claim 172, further comprising:
separating a gas or vapor from the ethylene rich stream and recirculating a portion of the gas or vapor to the reactor.

190. The method of claim 172, further comprising:
separating a stream containing hydrogen from the ethylene rich stream;
separating hydrogen from the stream containing hydrogen.

191. The method of claim 172, further comprising:
separating a gas or vapor from the ethylene rich stream and using at least a portion of the gas or vapor to at least partially quench the reactive product stream.

192. The method of claim 172, further comprising:
separating a liquid from the ethylene rich stream;
using at least a portion of the liquid to at least partially quench the reactive product stream.

193. The method of claim 182, further comprising:
conveying a portion of the light gases from which a portion of the hydrogen has been removed to the furnace as fuel.

194. The method of claim 172, further comprising: separating at least some ethylene from the light gas stream.

195. The method of claim 194, further comprising: conveying a portion of the light gases from which a portion of the ethylene has been removed to the furnace as fuel.

196. The method of claim 182, further comprising: conveying a portion of the hydrogen to the furnace as fuel.

197. The method of claim 172, further comprising: conveying a portion of the light gases to the reactor.

198. The method of claim 194, further comprising: conveying a portion of the ethylene to storage, to further processing, or to combinations thereof.

199. The method of claim 172, further comprising separating carbon dioxide from one or more sources within the process selected from the group comprising:
a portion of the reactive product stream;
a portion of the light gas stream;
a portion of the light gas stream after some ethylene has been removed;
a portion of the light gas stream after some hydrogen has been removed;
a portion of the hydrogenation reactor effluent.

200. The method of claim 199, further comprising conveying a portion of the light gas stream remaining after at least some carbon dioxide has been removed to the reactor.

201. The method of claim 172, further comprising separating hydrogen from the process and using a portion or portions of the hydrogen for one or more purposes selected from the group comprising:
recirculating back to the reactor;
conveying to the hydrogenation reactor;
generating electricity directly or indirectly;
burning as fuel;
exporting for external use.

202. The method of claim 172, further comprising separating hydrogen from one or more sources within the process selected from the group comprising:
a portion of the reactive product stream;
a portion of the improved reactive product stream;
a portion of the light gas stream;
a portion of the light gas stream after some ethylene has been removed;
a portion of the light gas stream after some carbon dioxide has been removed;
a portion of the light gas stream after some ethylene and carbon dioxide have been removed;
a portion of the hydrogenation reactor effluent.

203. The method of claim 172, further comprising separating a combustible gas or vapor from the process and using the gas or vapor as fuel.

204. The method of claim 172, further comprising separating a gas or vapor from the process and using the gas or vapor to generate electricity.

205. The method of claim 172, further comprising separating a combustible liquid or slurry from the process and using the liquid or slurry as fuel.

206. A method for converting natural gas to ethylene and reactive products, comprising:
providing a natural gas stream;
providing a feed stream comprising all or part of the natural gas stream;
conveying the feed stream to a reactor wherein the feed stream is heated using electrical power to a temperature and for a time sufficient to form a reactive product stream comprising acetylene, carbon dioxide, carbon monoxide and hydrogen;
quenching the reactive product stream;
separating from the reactive product stream an acetylene rich stream and a light gas stream, said light gas stream comprising carbon dioxide, carbon monoxide, and hydrogen;
conveying the acetylene rich stream to a hydrogenation reactor;
reacting acetylene and hydrogen in the hydrogenation reactor to form ethylene;
conveying a portion of the hydrogenation reactor effluent comprising ethylene to storage or further processing.

207. The method of claim 206, further comprising removing contaminants from the natural gas stream.

208. The method of claim 206, further comprising:
providing a second feed stream comprising a portion of the natural gas stream, a portion of a stream separated from the process, or both;
conveying the second feed stream to a reaction section of the reactor wherein the second feed stream is heated by intimate mixing with the feed stream to a temperature and for a time sufficient such that reactive products comprising acetylene, ethylene, or both, are produced;
wherein the feed stream is heated and not reacted, partially reacted, or completely reacted prior to mixing with the second feed stream; and
wherein the reactive products produced from the second feed stream are mixed with the reactive products produced from the feed stream to form an alternate reactive product stream.

209. The method of claim 206 wherein the pressure of the natural gas stream is between about 1 bar and about 20 bar.

210. The method of claim 206 wherein the natural gas stream is preheated to a temperature in the range of from about 400° K to about 1800° K.

211. The method of claim 206 wherein the feed stream is preheated to a temperature in the range of from about 400° K to about 1800° K.

212. The method of claim 211 wherein the feed stream is maintained at a temperature of at least 400° K for between about 0.1 and about 100 milliseconds.

213. The method of claim 212 wherein the feed stream is maintained at a temperature of at least 400° K for between about 0.2 and about 10 milliseconds.

214. The method of claim 206 wherein the natural gas stream, the feed stream, or both, is or are preheated by a device selected from the group consisting of electric arc, resistance heater, plasma generator, fuel cell, combustion heater, heat exchanger, and combinations thereof.

215. The method of claim 206 wherein the reactive product stream is quenched by a device selected from the group consisting of a Joule-Thompson expander, nozzle, turbo expander, water spray, hydrocarbon spray, oil spray, steam, boiler, heat exchanger, and combinations thereof.

216. The method of claim 206 wherein the reactive product stream is quenched at least partially by mixing the reactive product stream with vapor or liquid hydrocarbons.

217. The method of claim 206, further comprising separating carbon dioxide from one or more sources within the process selected from the group comprising:
a portion of the reactive product stream;
a portion of the light gas stream;
a portion of the light gas stream after some ethylene has been removed;
a portion of the light gas stream after some hydrogen has been removed;
a portion of the hydrogenation reactor effluent.

218. The method of claim 206, further comprising separating hydrogen from one or more sources within the process selected from the group comprising:
a portion of the reactive product stream;
a portion of the alternate reactive product stream;
a portion of the light gas stream;
a portion of the light gas stream after some ethylene has been removed;
a portion of the light gas stream after some carbon dioxide has been removed;
a portion of the light gas stream after some ethylene and carbon dioxide have been removed;
a portion of the hydrogenation reactor effluent.

219. The method of claim 206, further comprising separating hydrogen from the process and using a portion or portions of the hydrogen for one or more purposes selected from the group comprising:
recirculating back to the reactor;
conveying to the hydrogenation reactor;
generating electricity directly or indirectly;
burning as fuel;
exporting for external use.

220. The method of claim 206, further comprising segregating a portion of the natural gas stream for use in generating electricity directly or indirectly.

221. The method of claim 206, further comprising:
separating a gas or vapor from the hydrogenation reactor effluent and recirculating a portion of the gas or vapor to the reactor.

222. The method of claim 206, further comprising:
separating a stream containing hydrogen from the hydrogenation reactor effluent;
separating at least some hydrogen from the stream containing hydrogen.

223. The method of claim 206, further comprising:
separating a gas or vapor from the hydrogenation reactor effluent and using at least a portion of the gas or vapor to at least partially quench the reactive product stream.

224. The method of claim 206, further comprising:
separating a liquid from the hydrogenation reactor effluent.

225. The method of claim 224, further comprising:
using at least a portion of the liquid to at least partially quench the reactive product stream.

226. The method of claim 206, further comprising separating a combustible gas or vapor from the process and using the gas or vapor as fuel.

227. The method of claim 206, further comprising separating a gas or vapor from the process and using the gas or vapor to generate electricity.

228. The method of claim 206, further comprising separating a combustible liquid or slurry from the process and using the liquid or slurry as fuel.

229. A method for converting natural gas to reactive products, comprising:
providing a natural gas stream;
separating from the natural gas stream at least a methane rich stream and a methane lean stream;
providing a feed stream comprising light hydrocarbon gas or vapor;
conveying the feed stream to a reactor wherein the feed stream is heated to a temperature and for a time sufficient to form a reactive product stream comprising hydrogen, carbon dioxide, carbon monoxide and reactive products comprising acetylene, ethylene, or both;
quenching the reactive product stream;
separating from the reactive product stream an acetylene rich stream and a light gas stream, said light gas stream comprising carbon dioxide, carbon monoxide, and hydrogen;
conveying the acetylene rich stream to a hydrogenation reactor;
reacting acetylene and hydrogen in the hydrogenation reactor to form ethylene;
conveying an ethylene rich stream from the hydrogenation reactor to storage or further processing.

230. The method of claim 229, further comprising removing contaminants from the natural gas stream.

231. The method of claim 229, further comprising:
providing a second feed stream comprising a portion of the natural gas stream, a portion of a stream separated from the process, a portion of the methane rich stream, a portion of the methane lean stream, and combinations thereof;
conveying the second feed stream to a reaction section of the reactor wherein the second feed stream is heated by intimate mixing with the feed stream to a temperature and for a time sufficient such that reactive products comprising acetylene, ethylene, or both, are produced;
wherein the feed stream is heated and not reacted, partially reacted, or completely reacted prior to mixing with the second feed stream; and
wherein the reactive products produced from the second feed stream are mixed with the reactive products produced from the feed stream to form a reactive product stream.

232. The method of claim 229 wherein the feed stream comprises all or part of the methane rich stream.

233. The method of claim 229 wherein the feed stream comprises all or part of the methane lean stream.

234. The method of claim 229, further comprising burning or otherwise using a portion of the natural gas stream to heat the feed stream sufficient to form reactive products in the reactor.

235. The method of claim 229, further comprising burning or otherwise using a portion of the methane rich stream to heat the feed stream sufficient to form reactive products in the reactor.

236. The method of claim 229, further comprising burning or otherwise using a portion of the methane lean stream to heat the feed stream sufficient to form reactive products in the reactor.

237. The method of claim 229 wherein the reactive product stream is quenched at least partially by mixing the reactive product stream with a portion of the methane lean stream.

238. The method of claim 229 wherein the reactive product stream is quenched at least partially by mixing the reactive product stream with a portion of the natural gas stream.

239. The method of claim 229 wherein the reactive product stream is quenched at least partially by mixing the reactive product stream with vapor or liquid hydrocarbons.

240. The method of claim 229 wherein the feed stream comprises one or more light hydrocarbons selected from the group comprising methane, ethane, propane, butane, isobutane, and combinations thereof.

241. The method of claim 229 wherein a portion of the feed stream is converted to reactive products comprising acetylene, ethylene, or both, by means selected from the group comprising pyrolysis, partial oxidation, combustion, oxidative coupling, electric arc, resistance heater, plasma generator, catalytic conversion, and combinations thereof.

242. A method for converting gas comprising hydrocarbons to hydrocarbon liquids, comprising:

provinding a feed stream comprising light hydrocarbon gas or vapor;

conveying the feed stream to a reactor wherein the feed stream is heated to a temperature and for a time sufficient to form a reactive product stream comprising hydrogen, carbon dioxide, carbon monoxide and reactive products comprising acetylene, ethylene, or both;

quenching the reactive product stream;

separating from the reactive product stream an acetylene rich stream and a light gas stream, said light gas stream comprising carbon dioxide, carbon monoxide, and hydrogen;

conveying the acetylene rich stream to a hydrogenation reactor;

reacting acetylene and hydrogen in the hydrogenation reactor to form ethylene;

conveying an ethylene rich stream from the hydrogenation reactor to storage or further processing.

243. The method of claim 242 wherein the feed stream comprises one or more light hydrocarbons selected from the group comprising methane, ethane, propane, butane, isobutane, and combinations thereof.

244. The method of claim 242 wherein a portion of the feed stream is converted to reactive products comprising acetylene, ethylene, or both, by means selected from the group comprising pyrolysis, partial oxidation, combustion, oxidative coupling, electric arc, resistance heater, plasma generator, catalytic conversion, and combinations thereof.

* * * * *